US007959925B2

(12) United States Patent
Weinberg et al.

(10) Patent No.: US 7,959,925 B2
(45) Date of Patent: Jun. 14, 2011

(54) TRIMERIC OX40-IMMUNOGLOBULIN FUSION PROTEIN AND METHODS OF USE

(75) Inventors: Andrew D. Weinberg, Portland, OR (US); Nicholas P. Morris, Portland, OR (US); Carmen Romerdaue, Anchorage, AK (US)

(73) Assignee: Providence Health System, Seattle, WA (US)

( * ) Notice: Subject to any disclaimer, the term of this patent is extended or adjusted under 35 U.S.C. 154(b) by 0 days.

(21) Appl. No.: 12/618,678

(22) Filed: Nov. 13, 2009

(65) Prior Publication Data

US 2010/0136032 A1 Jun. 3, 2010

Related U.S. Application Data

(63) Continuation of application No. 11/418,940, filed on May 4, 2006, now abandoned.

(60) Provisional application No. 60/678,420, filed on May 6, 2005.

(51) Int. Cl.
*A61K 39/00* (2006.01)
*A61K 39/385* (2006.01)
*C12P 21/08* (2006.01)
*C07K 16/00* (2006.01)
*C07H 21/04* (2006.01)

(52) U.S. Cl. ............... 424/192.1; 424/178.1; 424/179.1; 424/185.1; 424/195.11; 424/198.1; 530/387.3; 530/388.22; 530/388.75; 536/23.4; 536/23.53

(58) Field of Classification Search ..................... None
See application file for complete search history.

(56) References Cited

U.S. PATENT DOCUMENTS

| | | | |
|---|---|---|---|
| 5,457,035 A | 10/1995 | Baum et al. | |
| 5,525,491 A * | 6/1996 | Huston et al. | 435/69.7 |
| 5,686,564 A * | 11/1997 | Brundish et al. | 530/327 |
| 5,783,665 A | 7/1998 | Baum et al. | |
| 6,242,566 B1 | 6/2001 | Godfrey et al. | |
| 6,312,700 B1 | 11/2001 | Weinberg | |
| 6,620,413 B1 * | 9/2003 | DeSauvage et al. | 424/178.1 |
| 6,936,439 B2 | 8/2005 | Mann et al. | |
| 7,179,468 B1 * | 2/2007 | Lu et al. | 424/188.1 |
| 7,238,499 B2 * | 7/2007 | Reddy | 435/69.7 |
| 7,271,149 B2 | 9/2007 | Glaesner et al. | |
| 2002/0054873 A1 | 5/2002 | Weinberg | |
| 2003/0100027 A1 | 5/2003 | Colyer et al. | |
| 2003/0119149 A1 | 6/2003 | Reddy | |
| 2003/0224991 A1 | 12/2003 | Dhanabal et al. | |
| 2004/0131587 A1 | 7/2004 | Thomas et al. | |

FOREIGN PATENT DOCUMENTS

| | | |
|---|---|---|
| WO | WO 95/12673 | 5/1995 |
| WO | WO 95/21915 | 8/1995 |

OTHER PUBLICATIONS

McWhirter et al. 1999. PNAS 99:8408-8413.*
Pullin et al. 1998. Biochem. 37:11836-11845.*
Calderhead et al. "Cloning of mouse Ox40: a T cell activation marker that may mediate T-B cell interactions," *J. Immunol.*, 151(10):5261-5271, 1993.
Gardnerova, et al., "The Use of TNF Family Ligands and Receptors and Agents which Modify their Interaction as Therapeutic Agents," *Current Drug Targets* 1:327-364, 2000.
Harbury et al. "A switch between two-, three-, and four-stranded coiled coils in GCN4 leucine zipper mutants," *Science*, 262(5138):1401-1407, 1993.
Haswell et al., "Analysis of the oligomeric requirement for signaling by CD40 using soluble multimeric forms of its ligand, CD154," *Eur. J Immunol.* 31:3094-3100, 2001.
International Search Report from related PCT Application No. PCT/US2006/017285, 4 pages, mailed Jan. 29, 2007.
Kelly et al., "Production of a Chimeric Form of CD23 that is Oligomeric and Blcoks IgE Binding to the FcβRI," *J. of Immunology*, 161:6696-6704, 1998.
Latza et al. "The human OX40 homolog: cDNA structure, expression and chromosomal assignment of the ACT35 antigen," *Eur. J. Immunol.*, 24(3):677-683, 1994.
Mallett et al. "Characterization of the MRC OX40 antigen of activated CD4 positive T lymphocytes—a molecule related to nerve growth factor receptor," *EMBO J.*, 9(4):1063-1068, 1990.
Miura et al., "Molecular Cloning and Characterization of a Novel Glycoprotein, gp34, that is Specifically Induced by the Human T-Cell Leukemia Virus Type I Transactivator p40$^{tax}$," Molecular and Cellular Biology 11(3):1313-1325, Mar. 1991.
Morris et al., *J. Biol Chem*, 274:418-423, 1999.
Ngo et al., The Protein Folding Problem and Tertiary Structure Prediction, 492-495, 1994.
Paterson et al. "Antigens of activated rat T lymphocytes including a molecule of 50,000 $M_r$ detected only on CD4 positive T blasts," *Mol. Immunol.*, 24(12):1281-1290, 1987.
Phillips, *J. Pharm Pharmacology*, 53:1169-1174, 2001.
Stark et al., "The use of trimeric isoleucine-zipper fusion proteins to study surface-receptor-ligand interactions in natural killer cells," *J. of Immunological Methods* 296:149-158, 2005.
Weinberg et al. "Selective depletion of myelin-reactive T cells with the anti-OX-40 antibody ameliorates autoimmune encephalomyelitis," *Nature Medicine*, 2(2):183-189, 1996.
Weinberg et al. "Target organ-specific up-regulation of the MRC OX-40 marker and selective production of Th1 lymphokine mRNA by encephalitogenic T helper cells isolated from the spinal cord of rats with experimental autoimmune encephalomyelitis," *J. Immunol.*, 152(9):4712-4721, 1994.
Weinberg et al., "Engagement of the OX-40 Receptor In Vivo Enhances Antitumor Immunity," *J. of Immunology*, 164:2160-2169, 2000.
Weissenhorn et al., "Assembly of a rod-shaped chimera of a trimeric GCN4 zipper and the HIV-1 pg41 ectodomain expressed in *Escherichia coli*," *Proc. Natl. Acad. Sci. USA*, 94:6065-6069, 1997.
Wells, *Biochemistry*, 29:8509-8517, 1990.
Morris et al., "Development and Characterization of Recombinant Human Fc:OX40L Fusion Protein Linked Via a Coiled-Coil Trimerization Domain," *Molecular Immunology* 44:3112-3121 (2007).

* cited by examiner

*Primary Examiner* — Shulamith H Shafer
(74) *Attorney, Agent, or Firm* — Klarquist Sparkman, LLP

(57) ABSTRACT

Compositions including a trimeric OX-40 fusion protein are disclosed. Also disclosed are methods for enhancing the immune response of a mammal to an antigen by engaging the OX-40 receptor on the surface of T-cells involving administering to the mammal a composition comprising a trimeric OX-40 fusion protein and a pharmaceutically acceptable carrier.

19 Claims, 7 Drawing Sheets

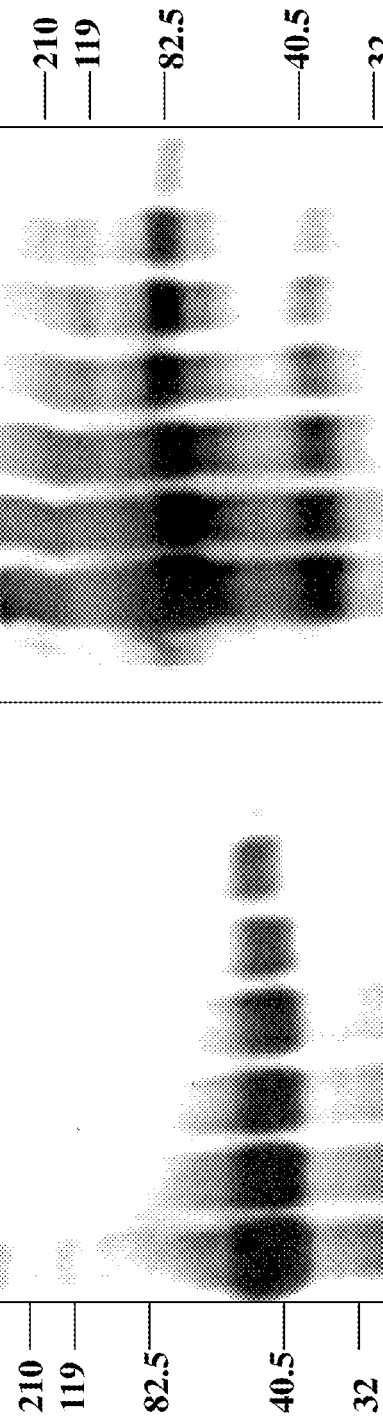
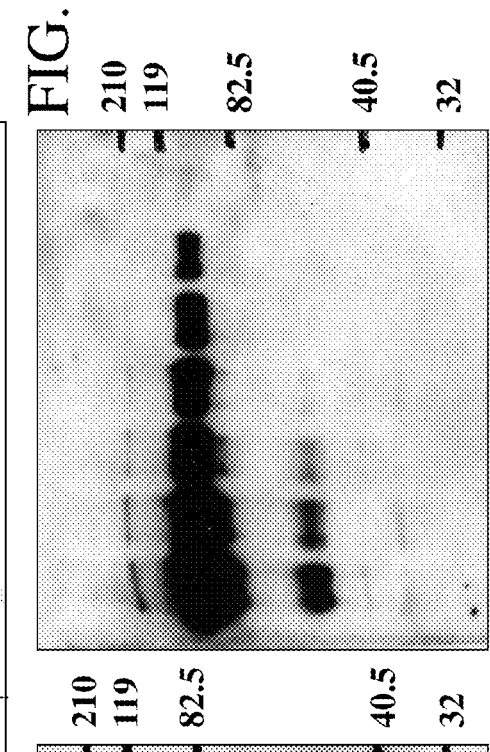
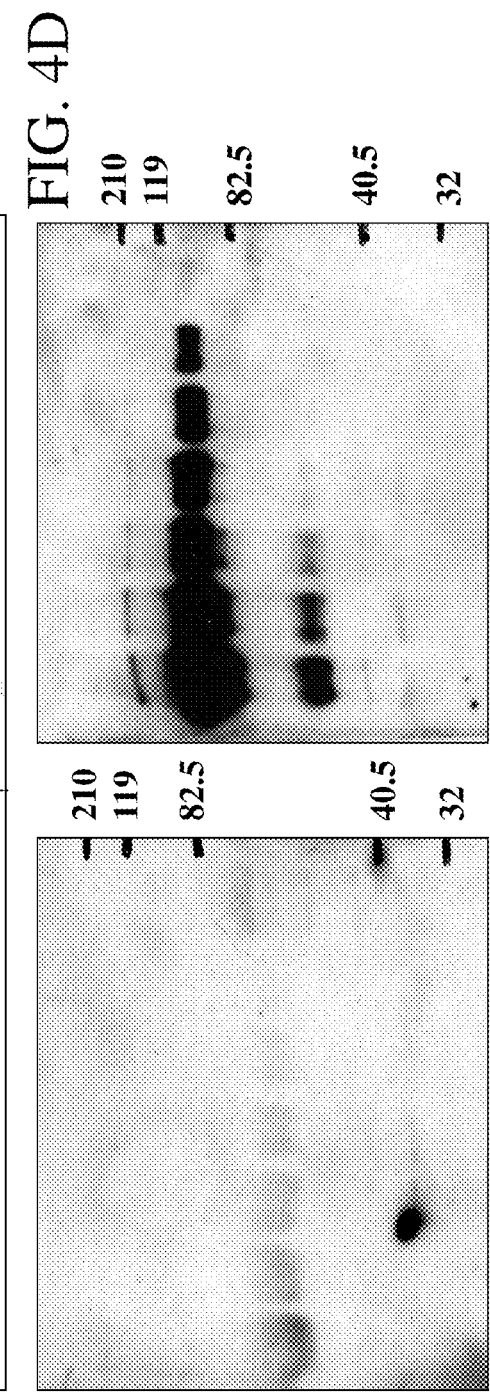
FIG. 4A
FIG. 4B
FIG. 4C
FIG. 4D

US 7,959,925 B2

SEQUENCE LISTING

<160> NUMBER OF SEQ ID NOS: 13

<210> SEQ ID NO 1
<211> LENGTH: 408
<212> TYPE: DNA
<213> ORGANISM: Homo sapiens
<220> FEATURE:
<221> NAME/KEY: misc_feature
<222> LOCATION: (1)..(408)
<223> OTHER INFORMATION: OX-40 receptor binding domain

<400> SEQUENCE: 1

```
caggtatcac atcggtatcc tcgatttcaa agtatcaaag tacaatttac cgaatataag      60
aaggagaaag gtttcatcct cacttcccaa aaggaggatg aaatcatgaa ggtgcagaac     120
aactcagtca tcatcaactg tgatgggttt tatctcatct ccctgaaggg ctacttctcc     180
caggaagtca acattagcct tcattaccag aaggatgagg agcccctctt ccaactgaag     240
aaggtcaggt ctgtcaactc cttgatggtg gcctctctga cttacaaaga caagtctac      300 ttgaatgtga ccactgacaa tacctccctg gatgacttcc atgtgaatgg cggagaactg     360
attcttatcc atcaaaatcc tggtgaattt tgtgtccttt aactcgag                  408
```

<210> SEQ ID NO 2
<211> LENGTH: 133
<212> TYPE: PRT
<213> ORGANISM: Homo sapiens
<220> FEATURE:
<221> NAME/KEY: misc_feature
<222> LOCATION: (1)..(133)
<223> OTHER INFORMATION: OX-40 receptor binding domain

<400> SEQUENCE: 2

```
Gln Val Ser His Arg Tyr Pro Arg Phe Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60
```

```
Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

<210> SEQ ID NO 3
<211> LENGTH: 135
<212> TYPE: DNA
<213> ORGANISM: Artificial sequence
<220> FEATURE:
<223> OTHER INFORMATION: isoleucine zipper domain

<400> SEQUENCE: 3
cttggtggcg gaagtatcaa acagatcgaa gataagattg aagagatctt gagcaaaatc      60
taccacattg aaaacgagat cgcgcgcatt aagaaactga tcggcgaacg tggccatggc     120
ggtgggtcga attca                                                     135

<210> SEQ ID NO 4
<211> LENGTH: 32
<212> TYPE: PRT
<213> ORGANISM: Artificial sequence
<220> FEATURE:
<223> OTHER INFORMATION: isoleucine zipper

<400> SEQUENCE: 4

Ile Lys Gln Ile Glu Asp Lys Ile Glu Glu Ile Leu Ser Lys Ile Tyr
1               5                   10                  15

His Ile Glu Asn Glu Ile Ala Arg Ile Lys Lys Leu Ile Gly Glu Arg
            20                  25                  30

<210> SEQ ID NO 5
<211> LENGTH: 691
<212> TYPE: DNA
<213> ORGANISM: Homo sapiens
<220> FEATURE:
<221> NAME/KEY: misc_feature
<222> LOCATION: (1)..(691)
<223> OTHER INFORMATION: immunoglobulin Fc domain

<400> SEQUENCE: 5
gctagcaacc gacaaaactc acacatgccc accgtgccca gcacctgaac tcctgggggg      60
accgtcagtc ttcctcttcc ccccaaaacc caaggacacc ctcatgatct cccggacccc     120
tgaggtcaca tgcgtggtgg tggacgtgag ccacgaagac cctgaggtca agttcaactg     180
gtacgtggac ggcgtggagg tgcataatgc caagacaaag ccgcgggagg agcagtacaa     240
cagcacgtac cgtgtggtca gcgtcctcac cgtcctgcac caggactggc tgaatggcaa     300
ggagtacaag tgcaaggtct ccaacaaagc cctcccagcc cccatcgaga aaaccatctc     360
caaagccaaa gggcagcccc gagaaccaca ggtgtacacc ctgcccccat cccgggagga     420
gatgaccaag aaccaggtca gcctgacctg cctggtcaaa ggcttctatc ccagcgacat     480
cgccgtggag tgggagagca atgggcagcc ggagaacaac tacaagacca cgcctcccgt     540
gctggactcc gacggctcct tcttcctcta tagcaagctc accgtggaca agagcaggtg     600
```

```
gcagcagggg aacgtcttct catgctccgt gatgcatgag gctctgcaca accactacac    660
gcagaagagc ctctccctgt ctccgggtaa a                                   691

<210> SEQ ID NO 6
<211> LENGTH: 230
<212> TYPE: PRT
<213> ORGANISM: Homo sapiens
<220> FEATURE:
<221> NAME/KEY: misc_feature
<222> LOCATION: (1)..(230)
<223> OTHER INFORMATION: immunoglobulin Fc domain

<400> SEQUENCE: 6

Leu Ala Thr Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225                 230

<210> SEQ ID NO 7
<211> LENGTH: 1240
<212> TYPE: DNA
<213> ORGANISM: Artificial sequence
<220> FEATURE:
<223> OTHER INFORMATION: polynucleotide encoding an OX-40 ligand fusion
      polypeptide

<400> SEQUENCE: 7
gctagcaacc gacaaaactc acacatgccc accgtgccca gcacctgaac tcctgggggg    60
accgtcagtc ttcctcttcc ccccaaaacc caaggacacc ctcatgatct cccggacccc   120
tgaggtcaca tgcgtggtgg tggacgtgag ccacgaagac cctgaggtca agttcaactg   180
gtacgtggac ggcgtggagg tgcataatgc caagacaaag ccgcgggagg agcagtacaa   240
```

```
cagcacgtac cgtgtggtca gcgtcctcac cgtcctgcac caggactggc tgaatggcaa      300
ggagtacaag tgcaaggtct ccaacaaagc cctcccagcc cccatcgaga aaaccatctc      360
caaagccaaa gggcagcccc gagaaccaca ggtgtacacc ctgcccccat cccgggagga      420
gatgaccaag aaccaggtca gcctgacctg cctggtcaaa ggcttctatc cagcgacat       480 cgccgtggag tgggagagca atgggcagcc ggagaacaac tacaagacca cgcctcccgt      540
gctggactcc gacggctcct tcttcctcta tagcaagctc accgtggaca agagcaggtg      600
gcagcagggg aacgtcttct catgctccgt gatgcatgag gctctgcaca accactacac      660
gcagaagagc ctctcccctgt ctccgggtaa agagctcctt ggtggcggaa gtatcaaaca     720
gatcgaagat aagattgaag agatcttgag caaaatctac cacattgaaa acgagatcgc      780
gcgcattaag aaactgatcg gcgaacgtgg ccatggcggt gggtcgaatt cacaggtatc      840
acatcggtat cctcgatttc aaagtatcaa agtacaattt accgaatata agaaggagaa      900
aggtttcatc ctcacttccc aaaaggagga tgaaatcatg aaggtgcaga caactcagt      960 catcatcaac tgtgatgggt tttatctcat ctccctgaag ggctacttct cccaggaagt     1020
caacattagc cttcattacc agaaggatga ggagcccctc ttccaactga gaaaggtcag     1080
gtctgtcaac tccttgatgg tggcctctct gacttacaaa gacaaagtct acttgaatgt    1140
gaccactgac aatacctccc tggatgactt ccatgtgaat ggcggagaac tgattcttat    1200
ccatcaaaat cctggtgaat tttgtgtcct ttaactcgag                            1240
```

<210> SEQ ID NO 8
<211> LENGTH: 410
<212> TYPE: PRT
<213> ORGANISM: Artificial sequence
<220> FEATURE:
<223> OTHER INFORMATION: OX-40 ligand fusion polypeptide

<400> SEQUENCE: 8

```
Leu Ala Thr Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190
```

-continued

```
Leu Thr Val Asp Lys Ser Arg Trp Gln Gln Gly Asn Val Phe Ser Cys
        195                 200                 205
Ser Val Met His Glu Ala Leu His Asn His Tyr Thr Gln Lys Ser Leu
    210                 215                 220
Ser Leu Ser Pro Gly Lys Glu Leu Leu Gly Gly Ser Ile Lys Gln
225                 230                 235                 240
Ile Glu Asp Lys Ile Glu Ile Leu Ser Lys Ile Tyr His Ile Glu
                245                 250                 255
Asn Glu Ile Ala Arg Ile Lys Lys Leu Ile Gly Glu Arg Gly His Gly
                260                 265                 270
Gly Gly Ser Asn Ser Gln Val Ser His Arg Tyr Pro Arg Phe Gln Ser
            275                 280                 285
Ile Lys Val Gln Phe Thr Glu Tyr Lys Lys Glu Lys Gly Phe Ile Leu
        290                 295                 300
Thr Ser Gln Lys Glu Asp Glu Ile Met Lys Val Gln Asn Asn Ser Val
305                 310                 315                 320
Ile Ile Asn Cys Asp Gly Phe Tyr Leu Ile Ser Leu Lys Gly Tyr Phe
                325                 330                 335
Ser Gln Glu Val Asn Ile Ser Leu His Tyr Gln Lys Asp Glu Glu Pro
            340                 345                 350
Leu Phe Gln Leu Lys Lys Val Arg Ser Val Asn Ser Leu Met Val Ala
        355                 360                 365
Ser Leu Thr Tyr Lys Asp Lys Val Tyr Leu Asn Val Thr Thr Asp Asn
    370                 375                 380
Thr Ser Leu Asp Asp Phe His Val Asn Gly Gly Glu Leu Ile Leu Ile
385                 390                 395                 400
His Gln Asn Pro Gly Glu Phe Cys Val Leu
                405                 410

<210> SEQ ID NO 9
<211> LENGTH: 408
<212> TYPE: DNA
<213> ORGANISM: Homo sapiens

<400> SEQUENCE: 9
caggtatcac atcggtatcc tcgaattcaa agtatcaaag tacaatttac cgaatataag        60
aaggagaaag gtttcatcct cacttcccaa aaggaggatg aaatcatgaa ggtgcagaac       120
aactcagtca tcatcaactg tgatgggttt tatctcatct ccctgaaggg ctacttctcc       180
caggaagtca acattagcct tcattaccag aaggatgagg agcccctctt ccaactgaag       240
aaggtcaggt ctgtcaactc cttgatggtg gcctctctga cttacaaaga caaagtctac       300
ttgaatgtga ccactgacaa tacctccctg gatgacttcc atgtgaatgg cggagaactg       360
attcttatcc atcaaaatcc tggtgaatta tgtgtccttt aactcgag                    408

<210> SEQ ID NO 10
<211> LENGTH: 28
<212> TYPE: DNA
<213> ORGANISM: Artificial sequence
<220> FEATURE:
<223> OTHER INFORMATION: oligonucleotide primer

<400> SEQUENCE: 10
gctagcaacc gacaaaactc acacatgc                                           28

<210> SEQ ID NO 11
<211> LENGTH: 24
<212> TYPE: DNA
```

```
<213> ORGANISM: Artificial sequence
<220> FEATURE:
<223> OTHER INFORMATION: oligonucleotide primer

<400> SEQUENCE: 11
ctcgagttaa agcacacaaa attc                                           24

<210> SEQ ID NO 12
<211> LENGTH: 63
<212> TYPE: DNA
<213> ORGANISM: Homo sapiens
<220> FEATURE:
<221> NAME/KEY: misc_feature
<222> LOCATION: (1)..(63)
<223> OTHER INFORMATION: secretory signal

<400> SEQUENCE: 12
atgagggcct ggatcttctt tctcctttgc ctggccggga gggctctggc agccccgcta    60 gcn                                                                  63

<210> SEQ ID NO 13
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: secretory signal

<400> SEQUENCE: 13

Met Arg Ala Trp Ile Phe Phe Leu Leu Cys Leu Ala Gly Arg Ala Leu
1               5                   10                  15

Ala Ala Pro Leu Ala
            20
```

TRIMERIC OX40-IMMUNOGLOBULIN FUSION PROTEIN AND METHODS OF USE

PRIORITY CLAIM

This is a continuation of U.S. patent application Ser. No. 11/418,940, filed on May 4, 2006, now abandoned. U.S. patent application Ser. No. 11/418,940 claims the benefit of U.S. Provisional Application No. 60/678,420, filed on May 6, 2005. Both of the prior applications are incorporated herein by reference in their entirety.

ACKNOWLEDGMENT OF GOVERNMENT SUPPORT

Aspects of the invention disclosed herein were made with support from the Government of the United States of America, pursuant to grants 5RO1CA102577 and 5R01CA109563 from the National Institutes of Health. The United States Government has certain rights in this invention.

FIELD

This disclosure relates to methods and compositions for generating enhanced immune responses in animals, particularly in human and non-human mammals. In particular, this disclosure relates to a trimeric OX-40 ligand fusion protein and to methods for its use. More generally, this disclosure relates to trimeric fusion proteins including a receptor binding (ligand) domain, a trimerization domain and a dimerization domain, such as an immunoglobulin Fc domain.

BACKGROUND

Numerous receptor-ligand interactions are involved in the induction, establishment and modulation of immune responses directed against antigens. At least two signals are necessary to activate a CD4 or CD8 T-cell response to antigen (Lenschow et al. (1996) *Ann. Rev. Immunol.* 14:233-258). The first signal is delivered through the T-cell receptor (TCR) by an antigen (typically a peptide) bound to a major histocompatibility (MHC) class I or II molecule present on the surface of an antigen presenting cell (APC). The second signal involves the binding of a ligand present on the surface of the APC to a second receptor molecule on the surface of the T-cell. This second signal is termed co-stimulation, and the APC ligand is often referred to as a co-stimulatory molecule.

During activation of CD4+ T-cells important co-stimulation is delivered by OX-40 receptor/OX-40 ligand interaction. The OX-40 receptor ("OX-40") (Paterson et al. (1987) *Mol. Immunol.* 24:1281-1290; Calderhead et al. (1993) *J. Immunol.* 151:5261-5271) has been shown to be present only on antigen activated CD4+ T-cells in vivo (Weinberg et al. (1994) *J. Immunol.* 152:4712-4721; Wienberg et al. (1996) *Nature Medicine* 2:183-189) unlike the CD28 receptor, which is present on the surface of many sub-classes of T-cells (irrespective of whether they are activated or not). For example, OX-40 is present on activated CD4+ T-cells that recognize autoantigen at the site of inflammation in autoimmune disease, but not in the periphery. OX-40 has also been shown to be present on the surface of a percentage of CD4+ T-cells isolated from tumor infiltrating lymphocytes and draining lymph node cells removed from patients with squamous cell tumors of the head and neck and melanomas (Vetto et al. (1997) *Am. J. Surg.* 174:258-265). The OX-40 ligand, a member of the tumor necrosis factor (TNF) superfamily, has been shown to co-stimulate T-cells which have been activated with an anti-CD3 antibody (i.e., in a nonantigen-specific manner) (Godfrey et al. (1994) *J. Exp. Med.* 180:757-762). Despite the recognition of the costimulatory properties of the OX-40 ligand, its benefits have not previously been fully exploited to enhance an antigen specific immune response.

SUMMARY

This disclosure relates to fusion polypeptides that include a ligand domain, a trimerization domain and an immunoglobulin Fc domain, which are capable of forming stable multimeric fusion proteins. Compositions and methods are provided that are useful for enhancing and maintaining an immune response of a mammal to an antigen. More specifically, this disclosure provides novel multimeric OX-40 ligand ("OX-40L") fusion proteins, as well as nucleic acids encoding polypeptides that form multimeric OX-40 ligand fusion proteins. This disclosure also provides methods of using trimeric OX-40 ligand fusion proteins to enhance and/or maintain an antigen specific immune response in a subject.

The invention is further detailed in the description, drawings and non-limiting examples set forth below.

BRIEF DESCRIPTION OF THE DRAWINGS

FIGS. 4A-D are western blots illustrating binding of anti-human IgG (A and B) and anti-human OX-40L antibodies (C and D) to purified protein. A and C illustrate blots of gels run under reducing conditions, whereas B and D illustrate blots of gels run under non-reducing conditions. A serial dilution is shown in each panel.

BRIEF DESCRIPTION OF SEQUENCE LISTING

Figure 1:
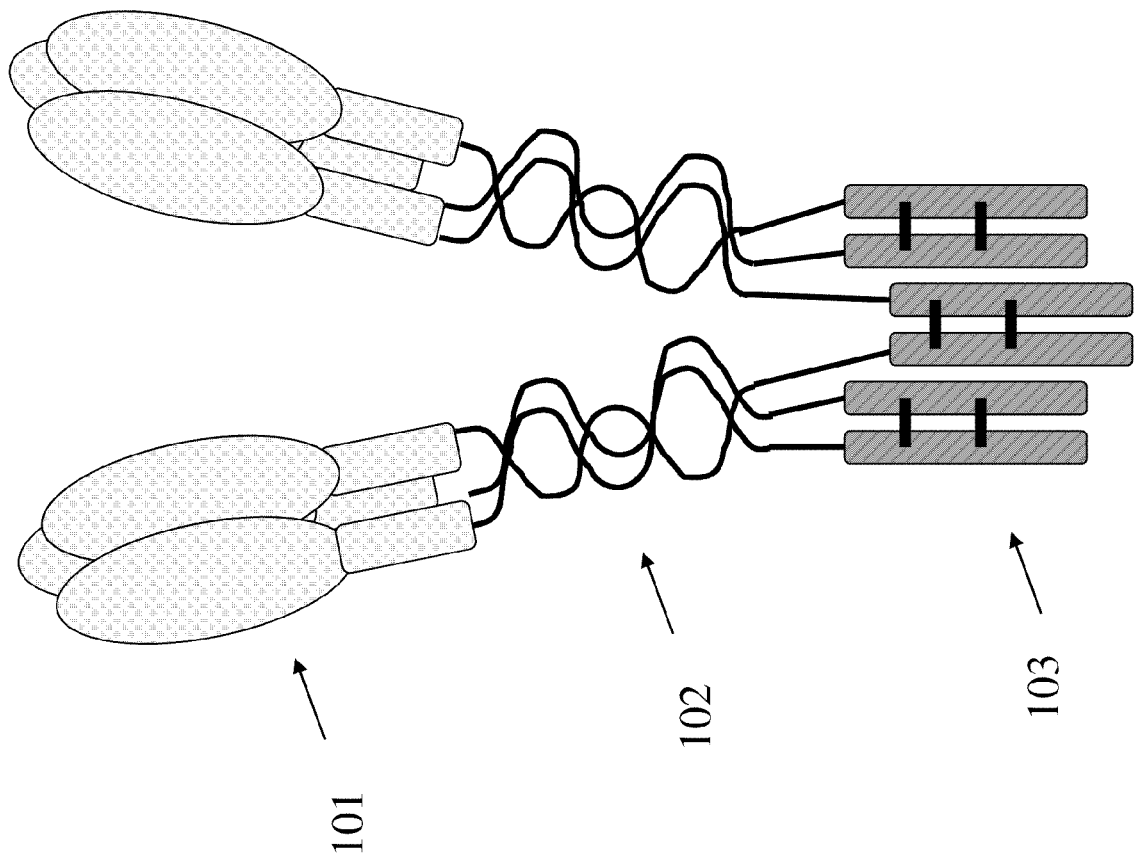
FIG. 1 schematically illustrates an exemplary multimeric protein, namely an OX-40L fusion protein.

The nucleic and amino acid sequences listed in the accompanying sequence listing are shown using standard letter abbreviations for nucleotide bases, and one letter code for amino acids, as defined in 37 C.F.R.1.822. Only one strand of each nucleic acid sequence is shown, but the complementary strand is understood as included by any reference to the displayed strand. All sequences designated herein by GEN-BANK® Accession No. refer to nucleic and amino acid sequences electronically accessible as of May 6, 2005.

SEQ ID NO: 1 is the polynucleotide sequence of a human OX-40 receptor binding domain.

SEQ ID NO: 2 is the amino acid sequence of a human OX-40 receptor binding domain.

SEQ ID NO: 3 is the polynucleotide sequence of an isoleucine zipper (ILZ) trimerization domain.

SEQ ID NO: 4 is the amino acid sequence of a yeast mutant Gcn4 isoleucine zipper (ILZ) trimerization domain.

SEQ ID NO: 5 is the polynucleotide sequence of a human immunoglobulin Fc domain.

SEQ ID NO: 6 is the amino acid sequence of a human immunoglobulin Fc domain.

SEQ ID NO: 7 is the polynucleotide sequence of a human OX-40 ligand fusion polypeptide.

SEQ ID NO: 8 is the amino acid sequence of a human OX-40 ligand fusion polypeptide.

SEQ ID NO: 9 is the sequence of the OX-40 ligand denoted as GENBANK® Accession No. NM 003326.

SEQ ID NO: 10 is the nucleotide sequence of the primer hFcγ1-5'.

SEQ ID NO: 11 is the nucleotide sequence of the primer hOX-40L-3'.

SEQ ID NO: 12 is the polynucleotide sequence of the human BM40 protein secretory signal.

SEQ ID NO: 13 is the amino acid sequence of the human BM40 protein secretory signal.

DETAILED DESCRIPTION

Introduction

Engagement of the OX-40 receptor on CD4+ T-cells during, or shortly after, priming by an antigen results in an increased response of the CD4+ T-cells to the antigen. In the context of the present disclosure, the term "engagement" refers to binding to and stimulation of at least one activity mediated by the OX-40 receptor. For example, engagement of the OX-40 receptor on antigen specific CD4+ T-cells results in increased T cell proliferation as compared to the response to antigen alone. The elevated response to the antigen can be maintained for a period of time substantially longer than in the absence of OX-40 receptor engagement. Thus, stimulation via the OX-40 receptor enhances the antigen specific immune response and increases resistance to disease by boosting T-cell recognition of antigens presented by infectious agents, such as bacteria and viruses, as well as tumor cells.

OX-40 receptor binding agents enhance antigen specific immune responses in a subject, such as a human subject, when administered to the subject during or shortly after priming of T-cells by an antigen. OX-40 receptor binding agents include OX-40 ligand ("OX-40L"), such as soluble extracellular ligand domains and OX-40L fusion proteins; anti-OX-40 antibodies (for example, monoclonal antibodies such as humanized monoclonal antibodies); and immunologically effective portions of anti-OX-40 antibodies. A specific example is a novel OX-40L fusion polypeptide that self-assembles into a multimeric (e.g., trimeric or hexameric) OX-40L fusion protein. The multimeric OX-40L fusion protein exhibits increased efficacy in enhancing antigen specific immune response in a subject, particularly a human subject, relative to previously described OX-40L fusion polypeptides. This increased activity results from the novel ability of this OX-40L fusion polypeptide to spontaneously assemble into highly stable trimers and hexamers. Also described are nucleic acids including polynucleotide sequences that encode such fusion polypeptides. This disclosure also provides methods for enhancing an antigen specific immune response in a subject using the multimeric OX-40L fusion polypeptides. The compositions and methods disclosed herein with respect to OX-40L fusion proteins can be more generally applied to the production and use of multimeric (e.g., trimeric and hexameric) receptor-binding fusion proteins.

SUMMARY OF SPECIFIC EMBODIMENTS

This disclosure relates to a multimeric OX-40L fusion protein that is useful for enhancing an antigen specific immune response in a subject, such as a human subject. A trimeric OX-40L fusion protein is composed of three OX-40L fusion polypeptides, each of which includes an OX-40 ligand domain, a trimerization domain and a dimerization domain, such as an immunoglobulin Fc domain. The trimerization domain promotes self-assembly of the expressed polypeptide by associating with two other trimerization domains to form a trimer. Upon assembly of the OX-40L fusion protein into a trimer, two Fc domains dimerize, and one Fc domain remains unpaired. The unpaired Fc domain associates with an unpaired Fc domain of a second OX-40L fusion protein trimer giving rise to a stable OX-40L fusion protein hexamer. For convenience, because the basic unit of this fusion protein is an assembly of three OX-40L fusion polypeptides, both the OX-40L fusion protein trimer and hexamer (formed from two OX-40L fusion protein trimers) are referred to herein as a "trimeric OX-40L fusion protein."

In an embodiment, the present disclosure provides a fusion polypeptide that includes in an N-terminal to C-terminal direction: an immunoglobulin Fc domain; a domain that induces trimerization of the fusion polypeptide (a "trimerization domain"); and an OX-40 receptor binding domain (FIG. 1). The fusion polypeptide forms a trimeric OX-40L fusion protein upon expression, which assembles into an active hexameric complex including two trimeric OX-40L fusion proteins. Within the trimeric OX-40L fusion protein, the Fc domain dimerizes, leaving one unpaired Fc polypeptide. The unpaired Fc domain in the fusion protein trimer is capable of interacting with the unpaired Fc domain of another OX-40L trimer acting as a dimerization domain between two OX-40L trimers and resulting in the formation of a hexamer (FIG. 1, and Holler et al., *Mol. Cell. Biol.* 23:1428, 2003). Thus, embodiments of the present disclosure include OX-40L fusion polypeptides that include in an N-terminal to C-terminal direction: a dimerization domain; a trimerization domain; and an OX-40 receptor binding domain. The fusion protein produced by assembly of this fusion polypeptide is capable of binding to, and stimulating at least one activity of, the OX-40 receptor. A particularly favorable attribute of this trimeric OX-40L fusion protein is its increased ability (as compared to previously described OX-40L fusion polypeptides) to stimulate activity, for example cellular proliferation, mediated via the OX-40 receptor.

Generally (but not necessarily), the OX-40 receptor binding domain and the immunoglobulin Fc domain are selected from a species that corresponds to that of the subject to which the fusion protein is to be administered. For example, if the subject is a human, optimal efficacy and minimal immunogenicity ("antigenicity") of the fusion protein can be achieved by administering a fusion protein with a human OX-40 receptor binding domain and a human Fc domain. Similarly, for example, if the subject is a non-human animal (e.g., a mammal), such as a mouse, a fusion protein made up of polypeptides that include a murine OX-40 receptor binding domain and a murine Fc domain can be administered. Likewise, for any other mammalian subject (e.g., veterinary subjects, including dogs, cats, horses, cows, pigs, sheep, goats, and non-human primates), the appropriate species specific OX-40 and immunoglobulin domains are included in a trimeric OX-40L fusion protein.

In an embodiment, the fusion polypeptide includes a trimerization domain that is an isoleucine zipper domain, for example, the isoleucine zipper domain represented by the amino acid sequence of SEQ ID NO: 4. In an embodiment, the OX-40 receptor binding domain is an extracellular domain of an OX-40 ligand. For example, the OX-40 receptor binding domain can be the extracellular domain of the human OX-40 ligand.

In addition to the receptor binding domain and the trimerization domain, the fusion polypeptides disclosed herein also include an immunoglobulin constant region domain. The constant region domain is typically an Fc domain. For example, the immunoglobulin constant region domain can include a human IgG constant region domain (e.g., the CH2 and CH3 domains), such as a human IgG1 Fc region. An exemplary amino acid sequence of an immunoglobulin Fc domain is provided in SEQ ID NO: 6.

In an embodiment, the fusion polypeptide is a polypeptide with the amino acid sequence represented by SEQ ID NO: 8. Fusion polypeptides with at least 95% sequence identity to SEQ ID NO: 8 are also included among the fusion polypeptides disclosed herein. For example, a fusion polypeptide encompassed by the present disclosure includes a fusion polypeptide with a sequence that is at least 96% identical to SEQ ID NO: 8. In an embodiment, the fusion polypeptide is at least 97% identical. In certain embodiments, the fusion polypeptide is as much as 98%, or even as much or greater than 99% identical to SEQ ID NO: 8. For example, a fusion polypeptide that forms a trimeric OX-40L fusion protein can include at least one amino acid deletion, addition or substitution relative to SEQ ID NO: 8, (or at most 2, 5 or 10 amino acid deletions, additions or substitutions relative to SEQ ID NO: 8). That is, a fusion polypeptide can include one amino acid deletion, addition or substitution relative to SEQ ID NO: 8, or it can include more than one (such as two, three, four or five) amino acid deletions, additions or substitutions relative to SEQ ID NO: 8. Typically, where a fusion polypeptide has an amino acid alteration (deletion, addition or substitution) relative to SEQ ID NO: 8, the function or activity of the polypeptide is not substantially altered with respect to the activity of the fusion polypeptide represented by SEQ ID NO: 8. For example, where an amino acid substitution is present, the amino acid substitution is most commonly a conservative amino acid substitution.

Another feature of the disclosure includes recombinant nucleic acids that encode an OX-40L fusion polypeptide, such as the polypeptide represented by SEQ ID NO: 8. The nucleic acids described herein encode OX-40L fusion polypeptides that possess the desirable characteristic of assembling into a trimeric OX-40L fusion protein that is capable of binding to and stimulating activity of the OX-40 receptor. In an embodiment, the fusion polypeptide is encoded by a nucleic acid with the polynucleotide sequence represented by SEQ ID NO: 7. In other embodiments, the fusion polypeptide is encoded by a related polynucleotide sequence that differs from SEQ ID NO: 7 by the deletion, addition or substitution of one or more nucleotides. For example, a nucleic acid that hybridizes under highly stringent conditions to a nucleic acid with the polynucleotide sequence of SEQ ID NO: 7. Typically, the nucleic acids are at least 95% identical to SEQ ID NO: 7. For example, a nucleic acid that encodes an OX-40L fusion polypeptide can be at least 96%, or at least 97%, or frequently at least 98%, or even 99% identical to SEQ ID NO: 7.

A recombinant nucleic acid that encodes an OX-40L fusion polypeptide in accordance with the present disclosure generally includes in a 5' to 3' direction: a polynucleotide sequence that encodes an immunoglobulin Fc domain; a polynucleotide sequence that encodes a trimerization domain; and a polynucleotide sequence that encodes an OX-40 receptor binding domain. The nucleic acids encode an OX-40L fusion polypeptide that includes in an N-terminal to C-terminal direction: an immunoglobulin Fc domain; a trimerization domain; and an OX-40 receptor binding domain.

As discussed above, it is generally desirable to select polynucleotide sequences that encode polypeptides (polypeptide domains) that correspond to the species of the subject to whom the encoded fusion proteins are to be administered. Thus, polynucleotide sequences encoding polypeptides having the amino acid sequence of human protein domains, for example, the human OX-40L receptor binding domain and a human immunoglobulin Fc domain are selected for administration to a human subject. In a similar manner, polynucleotide sequences that encode the polypeptide sequence found in any other species can be selected for administration to a subject of that species.

For example, in one embodiment, the nucleic acid encoding the OX-40L fusion polypeptide includes a polynucleotide sequence that encodes a human Ig Fc domain, such as a human IgG1 Fc domain. Typically, the polynucleotide sequence encodes one or both of a CH2 domain and a CH3 domain. For example, the polynucleotide sequence encoding the immunoglobulin domain can be the polynucleotide sequence represented by SEQ ID NO: 5.

The trimerization domain can be encoded by a polynucleotide sequence that encodes an isoleucine zipper domain, as indicated above. In an embodiment, the trimerization domain is an isoleucine zipper domain encoded by the polynucleotide sequence represented by SEQ ID NO: 3.

Typically, the OX-40 receptor binding domain is encoded by a polynucleotide sequence that encodes an extracellular domain of OX-40L. For example, the recombinant nucleic acid can include the polynucleotide sequence represented by SEQ ID NO: 1.

More generally, the disclosure can be applied to the production and use of trimeric fusion proteins that incorporate a receptor binding (e.g., ligand) domain, a trimerization domain and an immunoglobulin Fc domain. Such fusion proteins self-assemble into stable timers (and hexamers) with enhanced biological activities relative to other soluble forms of the ligand. For example, trimeric fusion proteins that include in an N-terminal to C-terminal direction: an immunoglobulin Fc domain; a trimerization domain; and a receptor binding domain. Typically, the receptor binding domain includes one or more domain (such as an extracellular domain) of a ligand that specifically binds to the receptor. Exemplary receptor binding domains that can be included in trimeric fusion proteins include TNF ligand domains, such as domains from the following ligands: TNF-a, TNF-b, Lymphotoxin-b, CD40L, FasL, CD27L, CD30L, 4-1BBL, TRAIL, RANK ligand, TWEAK, APRIL, BAFF, LIGHT, GITR ligand, EDA-A1, EDA-A2. Nucleic acids encoding these trimeric fusions can be produced and introduced into vectors as discussed below.

Another aspect of the disclosure relates to a method of enhancing an immune response in a subject. The method disclosed herein involves administering a trimeric OX-40L fusion protein to a subject who (or which) has been exposed to an antigen. Administration of the trimeric OX-40L fusion protein serves to enhance the antigen specific immune response (e.g., the antigen specific T-cell response) to the antigen. The subject can be a human subject, or a non-human subject. Typically, the non-human subject is a mammal (a veterinary subject), such as a dog, a cat, a horse, a cow, a pig, a sheep, a goat, or a non-human primate.

In an embodiment, the subject is exposed to the antigen prior to administration of the trimeric OX-40L fusion protein. Typically, if the subject is exposed to a soluble antigen prior to administration of the trimeric OX-40L fusion protein, the fusion protein is administered within about 10 days of exposure to the antigen. For example, the OX-40L fusion protein can be administered within about 7 days, for example within 24 to 48 hours, or within 3 days, or within about 7 days after exposure to the antigen. The exposure to the antigen can be brought about intentionally, for example, in the form of a vaccine. Alternatively, the exposure can be unintended, such as an environmental exposure to a pathogen (such as a bacterium, a virus, or a cellular or extracellular parasite), or the occurrence of a tumor. In another embodiment, the exposure to the antigen and administration of trimeric OX-40L fusion protein occur at the same time. If the exposure to the antigen and the administration of the trimeric OX-40L fusion protein occur simultaneously, the exposure (e.g., the intentional exposure) and administration of the trimeric fusion protein can be effected in a single formulation or pharmaceutical composition. Alternatively, the antigen and the trimeric OX-40L fusion protein can be administered in separate formulations.

In one embodiment, the trimeric OX-40L fusion protein is administered by expressing a recombinant nucleic acid encoding an OX-40L fusion polypeptide capable of trimerization in at least one cell of the subject. Upon expression in the cell(s) of the subject, the fusion polypeptides assemble into the trimeric OX-40L fusion protein. For example, a nucleic encoding the fusion polypeptide can be introduced into a cell (such as a cell, a mixed population of cells, or a purified population of cells removed from the subject) ex-vivo. The cell(s) comprising the recombinant nucleic acid are then introduced into the subject where the trimeric OX-40L fusion protein is expressed. The cell can be an autologous cell removed from the subject, or the cell can be a heterologous cell, such as a cell line (e.g., a cell line catalogued by the American Type Culture Collection, "ATCC").

In another embodiment, the OX-40L fusion protein is administered by introducing a vector (such as a bacterial plasmid or viral vector) including a nucleic acid encoding the fusion polypeptide, which assembles into the trimeric OX-40L fusion protein. For example, the vector can be an adenovirus vector, a retrovirus vector or a herpesvirus vector. If a viral vector is employed, it can be an attenuated or disabled virus, incapable of autonomous replication in the cells of the subject, thus, unable to cause a pathologic infection in the subject.

In some cases, the cell into which the recombinant nucleic acid encoding the trimeric OX-40L fusion protein is introduced is an antigen presenting cell (e.g., a B cell, a macrophage, a dendritic cell, etc.). The antigen can be an antigen of a pathogenic agent, such as a viral antigen, a bacterial antigen or an antigen of a parasite, or the antigen can be a tumor antigen. If the antigen is a tumor antigen, that is, an antigen expressed by or on a tumor cell, then the cell into which the recombinant nucleic acid encoding the trimeric OX-40L fusion protein is introduced can be a tumor cell (such as an autologous tumor cell obtained, e.g., following surgical removal or biopsy of a primary or metastatic tumor). Alternatively, a tumor cell line can be utilized, such as an immortalized or established tumor cell line. Typically, the cell line is selected to correspond to the type (i.e., origin, cell or tissue type) of tumor to be treated in the subject.

Additional details regarding the various embodiments are provided below.

TERMS

Unless otherwise explained, all technical and scientific terms used herein have the same meaning as commonly understood by one of ordinary skill in the art to which this disclosure belongs. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In order to facilitate review of the various embodiments of this disclosure, the following explanations of specific terms are provided:

The "OX-40 receptor" is a protein (also variously termed ACT-4 and ACT-35) expressed on the surface of antigen-activated mammalian $CD4^+$ T-cells (Weinberg et al. (1994) *J. Immunol.* 152:4712-4721; Weinberg et al. (1996) *Nature Medicine* 2:183-189; WO 95/12673; Latza et al. (1994) *Eur. J. Immunol.* 24:677-683). DNA sequences encoding mouse, rat and human OX-40 receptor homologs have been cloned and sequenced (Mallet et al. (1990) *EMBO J.* 9:1063-1068; Calderhead et al. (1993) *J. Immunol.* 151:5261-5271; Latza et al. (1994) *Eur. J. Immunol.* 24:677-683; WO 95/12673). Additionally, nucleotide and amino acid sequences for the human and mouse OX-40 receptors can be found in GEN-BANK® as Accession Nos. NM 003327 and NM 011659, respectively.

The "OX-40 ligand" ("OX-40L") (also variously termed gp34 and ACT-4-L) has been found expressed on the surface of certain mammalian cells, such as antigen presenting cells ("APCs"). OX-40L specifically binds to the OX-40 receptor. The human protein is described in PCT Publication No. WO 95/21915. The mouse OX-40L is described in U.S. Pat. No. 5,457,035. Polynucleotide and amino acid sequences of the human and mouse OX-40L are available in GENBANK® as Accession Nos. NM 003326 and NM 009452, respectively. The naturally occurring OX-40 ligand includes intracellular, transmembrane and extracellular domains. A functionally active soluble form of OX-40 ligand ("soluble OX-40 ligand") can be produced by deleting the intracellular and transmembrane domains as described, e.g., in U.S. Pat. Nos. 5,457,035 and 6,312,700, and WO 95/21915, the disclosures of which are incorporated herein for all purposes. A functionally active form of OX-40 ligand is a form that retains the capacity to bind specifically to the OX-40 receptor, that is, that possesses an OX-40 "receptor binding domain." Methods of determining the ability of an OX-40 ligand molecule or derivative to bind specifically to the OX-40 receptor are discussed below. Methods of making and using the OX-40 ligand and its derivatives (such as derivatives that include an OX-40 receptor binding domain) are described in WO 95/21915 (supra), which also describes proteins comprising the soluble form of OX-40 ligand linked to other peptides, such as human immunoglobulin ("Ig") Fc regions, that can be produced to facilitate purification of OX-40 ligand from cultured cells, or to enhance the stability of the molecule after in vivo administration to a mammal (see also, U.S. Pat. No. 5,457,035).

As used herein, the term "OX-40L" includes the entire OX-40 ligand, soluble OX-40 ligand, and functionally active portions of the OX-40 ligand. Also included within the definition of OX-40L are OX-40 ligand variants which vary in amino acid sequence from naturally occurring OX-40 ligand molecules but which retain the ability to specifically bind to an OX-40 receptor. Such variants are described in U.S. Pat. No. 5,457,035 and WO 95/21915 (supra).

An "OX-40 receptor binding agent" is an agent that binds substantially only to an OX-40 receptor, e.g., an OX-40 receptor present on the surface of antigen activated mammalian T-cells, such as activated $CD4^+$ T-cells. As used herein, the term "OX-40 receptor binding agent" includes anti-OX-40 antibodies and OX-40L. An OX-40 "receptor binding domain" is a domain that binds specifically to an OX-40 receptor.

A "trimerization domain" is an amino acid sequence within a polypeptide that promotes assembly of the polypeptide into trimers. For example, a trimerization can promote assembly into trimers via associations with other trimerization domains (of additional polypeptides with the same or a different amino acid sequence). The term is also used to refer to a polynucleotide that encodes such a peptide or polypeptide.

The term "Fc" domain refers to a portion of an antibody constant region. Traditionally, the term Fc domain refers to a protease (e.g., papain) cleavage product encompassing the paired CH2, CH3 and hinge regions of an antibody. In the context of this disclosure, the term Fc domain or Fc refers to any polypeptide (or nucleic acid encoding such a polypeptide), regardless of the means of production, that includes all or a portion of the CH2, CH3 and hinge regions of an immunoglobulin polypeptide.

The term "anti-OX-40 antibodies" encompasses monoclonal and polyclonal antibodies which are specific for OX-40, that is, which bind substantially only to OX-40 when assessed using the methods described below, as well as immunologically effective portions ("fragments") thereof. Immunologically effective portions of antibodies include Fab, Fab', $F(ab')_2$, Fabc and Fv portions (for a review, see Better and Horwitz (1989) "*Advances in Gene Technology: The Molecular Biology of Immune Disease and the Immune Response*" (*ICSU Short Reports*, Streilein et al. (eds.) vol. 10). In the present disclosure, immunologically effective portions of antibodies commonly include a heavy chain domain. Humanized forms of anti-OX-40 antibodies, e.g., monoclonal antibodies, and immunologically effective portions of anti-OX-40 antibodies are described in PCT Publication Nos. WO 95/12673 and WO 95/21915 (supra), along with methods which can be employed to produce such antibodies. Anti-OX-40 antibodies can also be produced using standard procedures described in a number of texts, including *Antibodies: A Laboratory Manual* by Harlow and Lane, Cold Spring Harbor Laboratory (1988).

More generally, an "antibody" or "immunoglobulin" (or an immunologically active portions of an immunoglobulin molecule) is a molecule that contains an antigen binding site that specifically binds (immunoreacts with) an antigen. A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the $V_L$ and $V_H$ domains of a single arm of an antibody, (iv) a dAb fragment (Ward et al. (1989) *Nature* 341:544-546) which consists of a $V_H$ domain; (v) an isolated complementarity determining region (CDR); and (vi) a $F(ab')_2$ fragment, a bivalent fragment comprising two Fab fragments linked by a disulfide bridge at the hinge region.

Methods of producing polyclonal and monoclonal antibodies are known to those of ordinary skill in the art, and many antibodies are available. See, for example, Coligan (1991) *Current Protocols in Immunology* Wiley/Greene, N.Y.; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495-497. Other suitable techniques for antibody preparation include selection of libraries of recombinant antibodies in phage or similar vectors. See, Huse et al. (1989) *Science* 246: 1275-1281; and Ward et al., (1989) *Nature* 341: 544-546. "Specific" monoclonal and polyclonal antibodies and antisera (or antiserum) will usually bind with a $K_D$ of at least about 0.1 µM, preferably at least about 0.01 µM or better, and most typically and preferably, 0.001 µM or better.

Immunoglobulins and certain variants thereof are known and many have been prepared in recombinant cell culture (e.g., see U.S. Pat. No. 4,745,055; U.S. Pat. No. 4,444,487; PCT Publication No. WO 88/03565; European Patent Nos. EP 256,654; EP 120,694; EP 125,023; Faoulkner et al. (1982) *Nature* 298:286; Morrison (1979) *J. Immunol.* 123:793; and Morrison et al. (1984) *Ann Rev. Immunol.* 2:239). Detailed methods for preparation of chimeric (humanized) antibodies can be found in U.S. Pat. No. 5,482,856. Additional details on humanization and other antibody production and engineering techniques can be found in Borrebaeck (ed) (1995) *Antibody Engineering, $2^{nd}$ Edition* Freeman and Company, NY; McCafferty et al. (1996) *Antibody Engineering, A Practical Approach* IRL at Oxford Press, Oxford, England; and Paul (1995) *Antibody Engineering Protocols* Humana Press, Towata, N.J.

The abbreviation "DNA" refers to deoxyribonucleic acid. DNA is a long chain polymer which comprises the genetic material of most living organisms (some viruses have genes comprising ribonucleic acid ("RNA"). The units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

A "cDNA" or "complementary DNA" is a piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from messenger RNA extracted from cells.

A "transformed" cell, or a "host" cell, is a cell into which a nucleic acid molecule has been introduced by molecular biology techniques. As used herein, the term transformation encompasses all techniques by which a nucleic acid molecule can be introduced into such a cell, including transfection with viral vectors, transformation with plasmid vectors, and introduction of naked DNA by electroporation, lipofection, and particle gun acceleration. A transformed cell or a host cell can be a bacterial cell or a eukaryotic cell.

An "isolated" biological component (such as a nucleic acid or protein) has been substantially separated or purified away from other biological components in the cell of the organism in which the component naturally occurs, such as, other chromosomal and extrachromosomal DNA and RNA, and proteins. Isolated nucleic acids and proteins include nucleic acids and proteins purified by standard purification methods. The term also embraces nucleic acids and proteins prepared by recombinant expression in a host cell as well as chemically synthesized nucleic acids.

The term "purified" does not require absolute purity; rather, it is intended as a relative term. Thus, for example, a purified OX-40 ligand preparation is one in which the OX-40 ligand is more pure than the ligand in its natural environment within a cell. Preferably, a preparation of an OX-40 ligand is purified such that the OX-40 ligand protein represents at least 50% of the total protein content of the preparation.

A "recombinant" nucleic acid is one that has a sequence that is not naturally occurring or that has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

The term "polynucleotide" or "nucleic acid" refers to a polymeric form of nucleotide at least 10 bases in length. The term polynucleotide "sequence" refers to the series of constituent nucleotides that make up a polynucleotide. The term polynucleotide sequence is also used to refer to the series of letters, e.g., a, c, g, t, that are used to represent a nucleic acid. A "recombinant" nucleic acid (e.g., a recombinant DNA) includes a genetic element (a polynucleotide sequence) that is not immediately contiguous with both of the genomic elements with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

A "vector" is nucleic acid molecule as introduced into a host cell, thereby producing a transformed host cell. A vector can include nucleic acid sequences that permit it to replicate in a host cell, such as an origin of replication. A vector can also include one or more selectable marker gene and other genetic elements known in the art.

A nucleic acid that regulates the expression of a heterologous polynucleotide sequence to which it is operably linked is referred to as an "expression control sequence" or a "transcription regulatory sequence." A transcription regulatory sequence is operably linked to a nucleic acid sequence when the regulatory sequence controls and regulates the transcription and, as appropriate, translation of the nucleic acid sequence. Thus, transcription regulatory sequences can include appropriate promoters, enhancers, transcription terminators, a start codon (typically, ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences.

A "promoter" is a minimal sequence sufficient to direct transcription of a nucleic acid. Also included are those promoter elements which are sufficient to render promoter-dependent gene expression controllable for cell-type specific, tissue-specific, or inducible by external signals or agents; such elements can be located in the 5' or 3' regions of the gene. Both constitutive and inducible promoters are included (see, e.g., Bitter et al. *Methods in Enzymology* (1987) 153:516-544). For example, when cloning in bacterial systems, inducible promoters such as pL of bacteriophage lambda, plac, pap, ptac (ptrp-lac hybrid promoter) and the like can be used. In one embodiment, when cloning in mammalian cell systems, promoters derived from the genome of mammalian cells (for example, metallothionein promoter) or from mammalian viruses (for example, the cytomegalovirus immediate early promoter, the retrovirus long terminal repeat; the adenovirus late promoter; the vaccinia virus 7.5K promoter) can be used. Promoters produced by recombinant DNA or synthetic techniques can also be used to provide for transcription of the nucleic acid sequences.

A first nucleic acid sequence is "operably linked" to a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame, for example, two polypeptide domains or components of a fusion protein.

A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

A "polypeptide" is any chain of amino acids, regardless of length or post-translational modification (for example, glycosylation or phosphorylation), such as a protein or a fragment or subsequence of a protein. The term "peptide" is typically used to refer to a chain of amino acids of between 3 and 30 amino acids in length. For example an immunologically relevant peptide can be between about 7 and about 25 amino acids in length, e.g., between about 8 and about 10 amino acids.

In the context of the present disclosure, a polypeptide can be a fusion polypeptide comprising a plurality of constituent polypeptide (or peptide) elements. Typically, the constituents of the fusion polypeptide are genetically distinct, that is, they originate from distinct genetic elements, such as genetic elements of different organisms or from different genetic elements (genomic components) or from different locations on a single genetic element, or in a different relationship than found in their natural environment. Nonetheless, in the context of a fusion polypeptide the distinct elements can be translated as a single polypeptide. The term monomeric fusion polypeptide (or monomeric fusion protein) is used synonymously with a single fusion polypeptide molecule to clarify reference to a single constituent subunit where the translated fusion polypeptides assume a multimeric tertiary structure or protein, e.g., a trimeric OX-40L fusion protein.

The term "mammal" includes both human and non-human mammals. Similarly, the term "subject" or "patient" includes both human and veterinary subjects or patients.

Trimeric OX-40L Fusion Proteins

Various formulations of OX-40 receptor binding agents have been described, including antibodies to the OX-40 receptor and a variety of OX-40L molecules. Such OX-40 receptor binding agents are useful for enhancing and maintaining an antigen specific immune response in a subject. For example, fusion proteins in which one or more domains of OX-40L are covalently linked to one or more additional protein domains can be administered to a subject with or following administration of (or exposure to) an antigen, to enhance the strength and/or duration of the antigen specific immune response. Exemplary OX-40L fusion proteins that can be used as OX-40 receptor binding agents are described in U.S. Pat. No. 6,312,700, the disclosure of which is incorporated herein for all purposes.

The present disclosure relates more specifically to an OX-40L fusion polypeptide that has the advantageous property of assembling into a trimeric form with an increased ability to stimulate human T cells relative to previously described OX-40L fusion polypeptides. An exemplary embodiment is illustrated schematically in FIG. 1. The OX-40L fusion polypeptide described herein possesses an OX-40L receptor binding domain 101, a trimerization domain 102, and a dimerization domain 103, such as an immunoglobulin (e.g., Fc) domain. Typically, the immunoglobulin domain, the trimerization domain and the OX-40L receptor binding domain are arranged in an N-terminal to C-terminal direction. An exemplary OX-40L fusion polypeptide is represented by SEQ ID NO: 8. Optionally, the fusion polypeptide can include one or more additional polypeptide sequence, such as a signal sequence (e.g., a secretory signal sequence), a linker sequence, an amino acid tag or label, or a peptide or polypeptide sequence that facilitates purification.

In an exemplary embodiment, the OX-40L receptor binding domain is an extracellular domain of a human OX-40L. The sequence of one such a domain is represented by SEQ ID NO: 2. However, any OX-40L polypeptide sequence that retains the desired property of binding to the OX-40 receptor is suitable in the fusion polypeptides and methods described herein.

Adjacent to (and most typically, contiguous with) the OX-40L receptor binding domain is a trimerization domain. The trimerization domain serves to promote self-assembly of individual OX-40L fusion polypeptide molecules into a trimeric protein. Thus, an OX-40L fusion polypeptide with a trimerization domain self-assembles into a trimeric OX-40L fusion protein. In one embodiment, the trimerization domain is an isoleucine zipper domain. An exemplary isoleucine zipper domain is the engineered yeast GCN4 isoleucine variant described by Harbury et al. (1993) Science 262:1401-1407, the disclosure of which is incorporated herein for all purposes. The sequence of one suitable isoleucine zipper domain is represented by SEQ ID NO: 4, although variants of this sequence that retain the ability to form a coiled-coil trimerization domain are equally suitable. Alternative coiled coil trimerization domains include: TRAF2 (GENBANK® Accession No. Q12933 [gi:23503103]; amino acids 299-348); Thrombospondin 1 (Accession No. PO7996 [gi:135717]; amino acids 291-314); Matrilin-4 (Accession No. O95460 [gi:14548117]; amino acids 594-618; CMP (matrilin-1) (Accession No. NP_002370 [gi:4505111]; amino acids 463-496; HSF1 (Accession No. AAX42211 [gi:61362386]; amino acids 165-191; and Cubilin (Accession No. NP_001072 [gi:4557503]; amino acids 104-138.

In addition to the OX-40L receptor binding domain and the trimerization domain, the fusion polypeptide includes an immunoglobulin domain, such as a constant region or "Fc" domain. The amino acid sequence of an exemplary immunoglobulin domain is provided in SEQ ID NO: 6, although numerous other immunoglobulin domain sequences can be used. In certain embodiments, the immunoglobulin domain serves as a dimerization domain that promotes assembly between two trimeric fusion polypeptides into a stable hexamer (that is a multimer that contains six OX-40L fusion polypeptides) via interactions between unpaired immunoglobulin domains (as shown schematically in FIG. 1). Optionally, alternative dimerization domains capable of forming stable interactions between the polypeptides that remain unpaired following trimerization of OX-40L fusion polypeptides can be used in place of the immunoglobulin domain.

The additional protein domains of the OX-40L fusion protein can serve a number of functions, including enhancing the activity of OX-40L, facilitating purification, and/or increasing the stability of the protein in the body of a subject. In the fusion proteins described herein, OX-40L, e.g., an extracellular domain of OX-40L, or other active fragment thereof, or a conservative or other variant of such a domain or fragment, can be fused with an immunoglobulin domain or other fusion protein domain that is selected to correspond to the subject to whom the OX-40L fusion polypeptide is to be administered. For example, if the intended subject is a human subject, it is desirable to select the Immunoglobulin domain from a human immunoglobulin protein or polypeptide. The specific example described below involves a fusion between OX-40L extracellular domain, a trimerization domain and a polypeptide including a constant domain of human IgG. Typically, the fusion polypeptide includes at least one immunoglobulin constant region domain. For example, the OX40L fusion polypeptide can include the CH2 and CH3 domains of IgG. In some embodiments, the fusion polypeptide includes a hinge amino acid sequence region corresponding to all or part of a hinge region of the IgG. Optionally, one or more cysteine residues can be mutated to non-sulfur amino acid residues, such as alanine or glycine. For example, by introducing altering the nucleotides "tgt" to "acc" (e.g., at position 8 in SEQ ID NO: 5 and SEQ ID NO: 7), a cysteine to threonine substitution can be introduced into the beginning of the Fc domain.

An exemplary OX-40L fusion polypeptide that assembles into a trimeric OX-40L fusion protein is further described in the Examples. The amino acid sequence of this fusion polypeptide is provided in SEQ ID NO: 8. Nonetheless, one of ordinary skill in the art will recognize that numerous other sequences also fulfill the criteria set forth herein for multimeric OX-40L fusion polypeptides. Thus, although multimeric OX-40L fusion polypeptides are predominantly described with respect to the polypeptide of SEQ ID NO: 8, numerous additional embodiments are encompassed by this disclosure.

In addition to the trimeric OX-40L fusion polypeptides and proteins described herein, functional fragments and variants are also a feature of this disclosure. A functional fragment or variant is a fragment or variant that maintains one or more functions of the reference polypeptide. The terms fragment and variant are not necessarily mutually exclusive. Functional fragments and variants can be of varying length. For example, some fragments have at least 10, 25, 50, 75, 100, or 200 amino acid residues. In general, the term "fragment" is used to refer to a subsequence of a polypeptide less than its entirety. The term "variant" is used to designate a polypeptide with one or more alterations or modifications with respect to a reference polypeptide, such as, the OX-40L fusion polypeptide explicitly described in detail in the examples. A variant can be identical in length to the reference polypeptide, or it can have one or more deletions or additions of amino acids. The variant can include deletions or additions of one or several amino acids, as long as the desired functional attribute (e.g., binding to the OX-40 receptor) is maintained. Additionally, a variant can include one or more amino acid substitutions. Generally, an amino acid substitution is a conservative substitution that replaces a naturally occurring amino acid with similar functional attributes.

One of ordinary skill in the art will recognize that a nucleic acid encoding a OX-40L fusion polypeptide can be altered or modified without materially altering one or more of the fusion protein's functions. As a preliminary matter, the genetic code is degenerate, and different codons can encode the same amino acid. More importantly, with respect to the encoded protein, even where an amino acid substitution is introduced, the mutation can be "conservative" and have no material impact on the essential functions of a protein. See Stryer (1988) *Biochemistry* 3rd Ed.

Modifications of a polypeptide that involve the substitution of one or more amino acids for amino acids having similar biochemical properties that do not result in change or loss of a biological or biochemical function of the polypeptide are designated "conservative" substitutions. These conservative substitutions are likely to have minimal impact on the activity of the resultant protein. Table 1 shows amino acids that can be substituted for an original amino acid in a protein, and which are regarded as conservative substitutions based on a BLOSUM similarity matrix.

| Amino Acid | Conservative Substitutions |
| --- | --- |
| G | A, S, N |
| P | E |
| D | S, K, Q, H, N, E |
| E | P, D, S, R, K, Q, H. N |
| N | G, D, E, T, S, R, K, Q, H |
| H | D, E, N, M, R, Q |
| Q | D, E, N, H, M, S, R, K |
| K | D, E, N, Q, R |
| R | E, N, H, Q, K |
| S | G, D, E, N, Q, A, T |
| T | N, S, V, A |
| A | G, S, T, V |
| M | H, Q, Y, F, L, I, V |
| V | T, A, M, F, L, I |
| I | M, V, Y, F, L |
| L | M, V, I, Y, F |
| F | M, V, I, L, W, Y |
| Y | H, M, I, L, F, W |
| W | F, Y |
| C | None |

One or more conservative changes, or up to ten conservative changes (e.g., two substituted amino acids, three substituted amino acids, four substituted amino acids, or five substituted amino acids, etc.) can be made in the polypeptide without changing a biochemical function of the OX-40L fusion polypeptide. Accordingly, OX-40L fusion polypeptides with one, two, three, four or five conservative amino acid substitutions are equivalents of the fusion polypeptide represented in SEQ ID NO: 8, or one or more domains or subportions thereof, such as SEQ ID NO: 2, SEQ ID NO: 4 and/or SEQ ID NO: 6. Thus, equivalent OX-40L fusion polypeptides include polypeptides with amino acid sequences that are at least 95% identical, such as 96%, or more than 97%, or even 98%, or 99% identical to SEQ ID NO: 8, or one or more domain thereof, such as SEQ ID NO: 2, SEQ ID NO: 4 and/or SEQ ID NO: 6. One of ordinary skill in the art will understand that the amino acid changes can be distributed throughout the length of SEQ ID NO: 8, or can be distributed within one or more subportions, e.g., domains of the fusion polypeptide.

For example, one or more conservative changes can be made in an OX-40L fusion polypeptide (including a trimeric OX-40L fusion polypeptide without changing its ability to bind to the OX-40 receptor. Similarly, one or more conservative changes can be made in an OX-40L fusion polypeptide without altering its ability to trimerize. More substantial changes in a biochemical function or other protein features can be obtained by selecting amino acid substitutions that are less conservative than those listed in Table 1. Such changes include, for example, changing residues that differ more significantly in their effect on maintaining polypeptide backbone structure (e.g., sheet or helical conformation) near the substitution, charge or hydrophobicity of the molecule at the target site, or bulk of a specific side chain. The following substitutions are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine) is substituted for (or by) one lacking a side chain (e.g., glycine).

Additionally, part of a polypeptide chain can be deleted without impairing or eliminating all of its functions. Similarly, insertions or additions can be made in the polypeptide chain, for example, adding epitope tags, without impairing or eliminating its functions (Ausubel et al. (1997) *J. Immunol.* 159:2502). Other modifications that can be made without materially impairing one or more functions of a polypeptide include, for example, in vivo or in vitro chemical and biochemical modifications that incorporate unusual amino acids. Such modifications include, for example, acetylation, carboxylation, phosphorylation, glycosylation, labeling, e.g., with radionuclides, and various enzymatic modifications, as will be readily appreciated by those of ordinary skill in the art. A variety of methods for labeling polypeptides and labels useful for such purposes are well known in the art, and include radioactive isotopes such as $^{32}P$, fluorophores, chemiluminescent agents, enzymes, and antiligands.

More generally, stable multimeric fusion proteins that include a domain selected from a ligand that binds a biologically relevant receptor can be produced in a manner analogous to that described herein with respect to OX-40 ligand. Such fusion proteins assemble into stable timers (and hexamers) with enhanced biological activity relative to other soluble forms of the ligand. The fusion proteins are characterized by the inclusion, in an N-terminal to C-terminal orientation, of an immunoglobulin (e.g., Fc) domain; a trimerization domain; and a receptor binding domain. While such fusion proteins can be made from essentially any ligand, they are especially useful for producing soluble counterparts for ligands that are multimeric (e.g., trimeric) in their active form. For example, trimeric fusion proteins can be favorably produced and employed that correspond to ligands that bind to receptors for members of the Tumor Necrosis Factor (TNF) family of proteins, such as: TNF-a, TNF-b, Lymphotoxin-b, CD40L, FasL, CD27L, CD30L, 4-1BBL, TRAIL, RANK ligand, TWEAK, APRIL, BAFF, LIGHT, GITR ligand, EDA-A1, EDA-A2.

Polynucleotides Encoding OX-40L Fusion Proteins

The OX-40L fusion polypeptides disclosed herein (such as the polypeptide represented by SEQ ID NO: 8) are encoded by novel polynucleotide sequences. Polynucleotide sequences that encode an OX-40L fusion polypeptide capable of trimerization include at least a first polynucleotide subsequence that encodes an immunoglobulin domain, at least a second polynucleotide subsequence that encodes a trimerization domain, and at least a third polynucleotide subsequence that encodes an OX-40L receptor binding domain. An exemplary polynucleotide sequence that encodes an OX-40L fusion polypeptide is represented by SEQ ID NO: 7. Typically, the polynucleotides encoding the immunoglobulin domain, the trimerization domain and the OX-40L receptor binding domains are joined in a 5' to 3' orientation. In one embodiment, the polynucleotides that encode the immunoglobulin (e.g., Fc) domain, the trimerization domain and the OX-40L domain are contiguously linked in a 5' to 3' orientation. Optionally, the polynucleotide encodes a signal sequence, e.g., a secretory signal sequence or a membrane localization sequence. In an embodiment, a polynucleotide sequence that encodes an amino acid linker sequence (e.g., a flexible linker sequence) is included in the polynucleotide that encodes the OX-40L fusion polypeptide.

For example, the nucleic acid that encodes the OX-40L fusion polypeptide favorably includes a polynucleotide sequence that encodes an OX-40 receptor binding domain that is an extracellular domain of a human OX-40L. An exemplary polynucleotide sequence is represented by SEQ ID NO: 1. The extracellular domain of the OX-40L represented by GENBANK® Accession No. NM 003326 (SEQ ID NO: 9), is equivalently suitable in the context of an OX-40L fusion polypeptide. SEQ ID NO: 1 and SEQ ID NO: 9 represent functionally equivalent polynucleotide sequences of the human OX-40L. SEQ ID NO: 1 possesses two nucleotide substitutions, each of which is an A to T substitution. The polypeptide represented by SEQ ID NO: 2 includes a substitution of a phenylalanine for an isoleucine at amino acid position 9 with respect to the GENBANK® sequence. Similarly, any polynucleotide sequence that encodes a functionally equivalent OX-40L domain can be employed in the fusion polypeptides described herein.

Adjacent to the polynucleotide sequence encoding the OX-40L receptor binding domain is a polynucleotide sequence encoding a trimerization domain. As indicated above, one favorable trimerization domain is an isoleucine zipper domain. In one favorable embodiment, the nucleic acid encoding the OX-40L fusion polypeptide includes a polynucleotide sequence that encodes an isoleucine zipper domain. An exemplary polynucleotide sequence is provided in SEQ ID NO: 3. Alternative trimerization domains include those of TRAF2, Thrombospondin 1, Matrilin-4, CMP, HSF1 and Cubilin.

In addition to polynucleotide sequences that encode an OX-40L receptor binding domain and a trimerization domain, the nucleic acid that encodes the OX-40L fusion polypeptide also includes a polynucleotide sequence that encodes an immunoglobulin constant region domain ("Fc domain"). Typically the polynucleotide encodes the CH2, CH3 and hinge domains of a human immunoglobulin Fc region, although other constant region domains, e.g., the CH2 and CH1 domains, could be substituted. In an exemplary embodiment, the polynucleotide encodes an IgG1 Fc domain. Favorably, the immunoglobulin domain is capable of promoting dimerization (e.g., with another polypeptide including an immunoglobulin domain). An exemplary polynucleotide sequence that encodes a human IgG1 Fc domain is provided in SEQ ID NO: 5.

Polynucleotides encoding the OX-40L fusion polypeptides include deoxyribonucleotides (DNA, cDNA) or ribodeoxynucletides (RNA) sequences, or modified forms of either nucleotide, which encode the fusion polypeptides described herein. The term includes single and double stranded forms of DNA and/or RNA.

Polynucleotide sequences described herein include polynucleotide sequences, such as the sequences represented by SEQ ID NO: 7, which encode OX-40L fusion polypeptides, as well as polynucleotide sequences complementary thereto. For example, a polynucleotide that encodes an OX-40L fusion polypeptide sequence represented by SEQ ID NO: 8 is a feature of this disclosure.

In addition to SEQ ID NOs: 1, 3, 5, 7 and 9, polynucleotide sequences that are substantially identical to these polynucleotide sequences can be used in the compositions and methods of the disclosure. Fore example, a substantially identical polynucleotide sequence can have one or a small number of deletions, additions and/or substitutions. Such polynucleotide changes can be contiguous or can be distributed at different positions in the nucleic acid. A substantially identical polynucleotide sequence can, for example, have 1, or 2, or 3, or 4, or even more nucleotide deletions, additions and/or substitutions. Typically, the one or more deletions, additions and/or substitutions do not alter the reading frame encoded by the polynucleotide sequence, such that a modified ("mutant") but substantially identical polypeptide is produced upon expression of the nucleic acid.

The similarity between amino acid (and/or polynucleotide) sequences is expressed in terms of the similarity between the sequences, otherwise referred to as sequence identity. Sequence identity is frequently measured in terms of percentage identity (or similarity); the higher the percentage, the more similar are the primary structures of the two sequences. Thus, a polynucleotide that encodes an OX-40L fusion polypeptide can be at least about 95%, or at least 96%, frequently at least 97%, 98%, or 99% identical to SEQ ID NO: 7 (or SEQ ID NO: 9) or to at least one subsequence thereof, such as SEQ ID NO: 1, SEQ ID NO: 3 and/or SEQ ID NO: 5). Methods of determining sequence identity are well known in the art. Various programs and alignment algorithms are described in: Smith and Waterman, *Adv. Appl. Math.* (1981) 2:482; Needleman and Wunsch (1970) *J. Mol. Biol.* 48:443; Higgins and Sharp (1988) *Gene* 73:237; Higgins and Sharp (1989) *CABIOS* 5:151; Corpet et al. (1988) *Nucleic Acids Research* 16:10881; and Pearson and Lipman (1988) *Proc. Natl. Acad. Sci. USA* 85:2444. Altschul et al. (1994) *Nature Genet.* 6:119, presents a detailed consideration of sequence alignment methods and homology calculations.

The NCBI Basic Local Alignment Search Tool (BLAST) (Altschul et al., *J. Mol. Biol.* (1990) 215:403) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Thus, a sequence (that is a polynucleotide or polypeptide sequence) that is substantially identical, or substantially similar polynucleotide to a polynucleotide of SEQ ID NO: 1, 3, 5, 7 or 9 (or to a polypeptide sequence of SEQ ID NO: 2, 4, 6, or 8) is encompassed within the present disclosure. A sequence is substantially identical to one of SEQ ID NOs: 1-9 if the sequence is identical, on a nucleotide by nucleotide basis, with at least a subsequence of the reference sequence (e.g., SEQ ID NOs: 1-9). Such polynucleotides can include, e.g., insertions, deletions, and substitutions relative to any of SEQ ID NOs: 1, 3, 5, 7, and/or 9. For example, such polynucleotides are typically at least about 70% identical to a reference polynucleotide (or polypeptide) selected from among SEQ ID NO: 1 through SEQ ID NO: 9. That is, at least 7 out of 10 nucleotides (or amino acids) within a window of comparison are identical to the reference sequence selected SEQ ID NO: 1-9. Frequently, such sequences are at least about 80%, usually at least about 90%, and often at least about 95%, or more identical to a reference sequence selected from SEQ ID NO: 1 to SEQ ID NO: 9. For example, the amino acid or polynucleotide sequence can be 96%, 97%, 98% or even 99% identical to the reference sequence, e.g., at least one of SEQ ID NO: 1 to SEQ ID NO: 9

Another indicia of sequence similarity between two nucleic acids is the ability to hybridize. The more similar are the sequences of the two nucleic acids, the more stringent the conditions at which they will hybridize. Substantially similar or substantially identical nucleic acids to SEQ ID NO: 7 (and to subsequences thereof, such as SEQ ID NO: 1, SEQ ID NO: 3 and SEQ ID NO: 5) include nucleic acids that hybridize under stringent conditions to any of these reference polynucleotide sequences. Thus, a nucleic acid that hybridizes under stringent conditions to a reference polynucleotide sequence selected from among SEQ ID NOs: 1, 3, 5, and/or 7 is substantially identical or substantially similar to the polynucleotides encoding OX-40L fusion polypeptides described herein.

The stringency of hybridization conditions are sequence-dependent and are different under different environmental parameters. Thus, hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al. (2001) *Molecular Cloning: A Laboratory Manual*, Cold Spring Harbor Laboratory Press, Cold Spring Harbor, N.Y.; Tijssen (1993) *Hybridization With Nucleic Acid Probes, Part I: Theory and Nucleic Acid Preparation*, Laboratory Techniques in Biochemistry and Molecular Biology, Elsevier Science Ltd., NY and Ausubel et al. (1999) *Short Protocols in Molecular Biology*, 4$^{th}$ ed., John Wiley & Sons, Inc.

For purposes of the present disclosure, "stringent conditions" encompass conditions under which hybridization will only occur if there is less than 25% mismatch between the hybridization molecule and the target sequence. "Stringent conditions" can be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. In contrast nucleic acids that hybridize under "low stringency conditions include those with much less sequence identity, or with sequence identity over only short subsequences of the nucleic acid.

For example, in nucleic acid hybridization reactions, the conditions used to achieve a particular level of stringency will vary depending on the nature of the nucleic acids being hybridized. The length, degree of complementarity, nucleotide sequence composition (e.g., GC v. AT content), and nucleic acid type (e.g., RNA versus DNA) of the hybridizing regions of the nucleic acids all influence the selection of appropriate hybridization conditions. Additionally, whether one of the nucleic acids is immobilized, for example, on a filter can impact the conditions required to achieve the desired stringency.

A specific example of progressively higher stringency conditions is as follows: 2×SSC/0.1% SDS at about room temperature (hybridization conditions); 0.2×SSC/0.1% SDS at about room temperature (low stringency conditions); 0.2× SSC/0.1% SDS at about 42° C. (moderate stringency conditions); and 0.1×SSC at about 68° C. (high stringency conditions). One of skill in the art can readily determine variations on these conditions (e.g., with reference to Sambrook, Tjissen and/or Ausubel, cited above). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Additionally, the nucleic acid encoding the OX-40L fusion polypeptides can also include polynucleotide sequences, such as expression regulatory sequences and/or vector sequences that facilitate the expression or replication of the nucleic acids. Similarly, the nucleic acid encoding the OX-40L fusion polypeptide can include additional coding sequences that confer functional attributes on the encoded polypeptide. Such sequences include secretory signal sequences and membrane localization signals.

Nucleic acids encoding OX-40L fusion polypeptides can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR or other in vitro amplification. These procedures are well known to those of ordinary skill in the art, and exemplary protocols can be found, e.g., in Sambrook and Ausubel (supra).

A polynucleotide sequence (or portions derived from it) such as a cDNA encoding an OX-40L fusion polypeptide can be introduced into a vector, such as a eukaryotic expression vector, by conventional techniques. An expression vector is designed to permit the transcription of the polynucleotide sequence encoding the OX-40L fusion polypeptide in cells by providing regulatory sequences that initiate and enhance the transcription of the cDNA and ensure its proper splicing and polyadenylation. Numerous expression vectors are known to those of skill in the art, and are available commercially, or can be assembled from individual components according to conventional molecular biology procedures, such as those described in, e.g., Sambrook and Ausubel, cited above. The pCEP D4-7 vector described in the Examples is one such suitable expression vector.

For example, the cytomegalovirus ("CMV") immediate early promoter can favorably be utilized to regulate transcription of an OX-40L fusion polypeptide upon introduction of an expression vector containing a polynucleotide encoding the OX-40L fusion polypeptide operably linked to the CMV promoter. Additionally, vectors containing the promoter and enhancer regions of the SV40 or long terminal repeat (LTR) of the Rous Sarcoma virus and polyadenylation and splicing signal from SV40 are readily available (Mulligan et al. (1981) *Proc. Natl. Acad. Sci. USA* 78:1078-2076; Gorman et al. (1982) *Proc. Natl. Acad. Sci. USA* 78:6777-6781). The level of expression of the polynucleotide that encodes a polypeptide can be manipulated with this type of vector, either by using promoters that have different activities (for example, the baculovirus pAC373 can express cDNAs at high levels in *S. frugiperda* cells (Summers and Smith (1985) In *Genetically Altered Viruses and the Environment*, Fields et al. (Eds.) 22:319-328, CSHL Press, Cold Spring Harbor, N.Y.) or by using vectors that contain promoters amenable to modulation, for example, the glucocorticoid-responsive promoter from the mouse mammary tumor virus (Lee et al. (1982) *Nature* 294:228).

In addition, some vectors contain selectable markers such as the gpt (Mulligan and Berg (1981) *Proc. Natl. Acad. Sci. USA* 78:2072-2076) or neo (Southern and Berg (1982) *J. Mol. Appl. Genet.* 1:327-341) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al. (1981) *Mol. Cell. Biol.* 1:486) or Epstein-Barr (Sugden et al. (1985) *Mol. Cell. Biol.* 5:410). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al. (1978) *J. Biol. Chem.* 253:1357).

Vector systems suitable for the expression of polynucleotides encoding fusion proteins include, in addition to the specific vectors described in the examples, the pUR series of vectors (Ruther and Muller-Hill (1983) *EMBO J.* 2:1791), pEX1-3 (Stanley and Luzio (1984) *EMBO J.* 3:1429) and pMR100 (Gray et al. (1982) *Proc. Natl. Acad. Sci. USA* 79:6598). Vectors suitable for the production of intact native proteins include pKC30 (Shimatake and Rosenberg (1981) *Nature* 292:128, 1981), pKK177-3 (Amann and Brosius (1985) *Gene* 40:183) and pET-3 (Studiar and Moffatt (1986) *J. Mol. Biol.* 189:113).

The present disclosure, thus, encompasses recombinant vectors that comprise all or part of the polynucleotides encoding trimeric OX-40L fusion proteins or cDNA sequences encoding OX-40L fusion polypeptides, for expression in a suitable host, either alone or as a labeled or otherwise detectable protein. The DNA is operably linked in the vector to an expression control sequence in the recombinant DNA molecule so that the fusion polypeptide or protein can be expressed. The expression control sequence can be selected from the group consisting of sequences that control the expression of genes of prokaryotic or eukaryotic cells and their viruses and combinations thereof. The expression control sequence can be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The nucleic acid encoding an OX-40L fusion polypeptide can also be transferred from its existing context to other cloning vehicles, such as other plasmids, bacteriophages, cosmids, animal viruses and yeast artificial chromosomes (YACs) (Burke et al. (1987) *Science* 236:806-812). These vectors can then be introduced into a variety of hosts including somatic cells, and simple or complex organisms, such as bacteria, fungi (Timberlake and Marshall (1989) *Science* 244: 1313-1317), invertebrates, plants (Gasser and Fraley (1989) *Science* 244:1293), and animals (Pursel et al. (1989) *Science* 244:1281-1288), which cell or organisms are rendered transgenic by the introduction of the heterologous cDNA.

For expression in mammalian cells, a cDNA sequence can be ligated to heterologous promoters, such as the simian virus (SV) 40 promoter in the pSV2 vector (Mulligan and Berg (1981) *Proc. Natl. Acad. Sci. USA* 78:2072-2076), and introduced into cells, such as monkey COS-1 cells (Gluzman (1981) *Cell* 23:175-182), to achieve transient or long-term expression. The stable integration of the chimeric gene construct can be maintained in mammalian cells by biochemical selection, such as neomycin (Southern and Berg (1982) *J. Mol. Appl. Genet.* 1:327-341) and mycophenolic acid (Mulligan and Berg (1981) *Proc. Natl. Acad. Sci. USA* 78:2072-2076).

Production of Recombinant OX-40L Fusion Proteins

OX-40L fusion proteins can be made in any suitable heterologous expression system, and, where appropriate, the DNA encoding the fusion protein can also encode a known secretory signal sequence suitable for the host cell system employed so that the DNA is translated into a protein that at first includes the secretory signal and the cleavage sequence but is then transported out of the cell without such ancillary sequences.

The expression and purification of proteins, such as a trimeric OX-40L fusion protein, can be performed using standard laboratory techniques. Examples of such methods are discussed or referenced herein. After expression, purified proteins have many uses, including for instance functional analyses, antibody production, and diagnostics, as well as the prophylactic and therapeutic uses described below. Partial or full-length cDNA sequences, which encode the fusion proteins, can be ligated into bacterial expression vectors. Methods for expressing large amounts of protein from a cloned sequence introduced into *Escherichia coli* (*E. coli*) or baculovirus/Sf9 cells can be utilized for the purification, localization and functional analysis of proteins, as well as for the production of antibodies and vaccine compositions. For example, fusion proteins consisting of an OX-40L fusion polypeptide can be used in various procedures, for instance to prepare polyclonal and monoclonal antibodies against these proteins. Thereafter, these antibodies can be used to purify proteins by immunoaffinity chromatography, in diagnostic assays to quantitate the levels of protein and to localize proteins in tissues and individual cells by immunofluorescence. More particularly, the fusion proteins and the polynucleotides encoding them described herein can be used to produce pharmaceutical compositions, including vaccine compositions suitable for prophylactic and/or therapeutic administration.

Methods and additional plasmid vectors for producing the polynucleotides encoding fusion proteins and for expressing these polynucleotides in bacterial and eukaryotic cells are well known in the art, and specific methods are described in Sambrook (supra). Such fusion proteins can be made in large amounts, are easy to purify, and can be used to enhance an immune response, including an antibody response or a T-cell response. Native proteins can be produced in bacteria by placing a strong, regulated promoter (such as the CMV promoter) and an efficient ribosome-binding site upstream of the cloned gene. If low levels of protein are produced, additional steps can be taken to increase protein production; if high levels of protein are produced, purification is relatively easy. Suitable methods are presented in Sambrook (supra), and are well known in the art. Often, proteins expressed at high levels are found in insoluble inclusion bodies. Methods for extracting proteins from these aggregates are described by Sambrook (supra). Proteins, including fusion proteins, can be isolated from protein gels, lyophilized, ground into a powder and used as an antigen.

The transfer of DNA into eukaryotic, in particular human or other mammalian cells, is now a conventional technique known to those of ordinary skill in the art. The vectors are introduced into the recipient cells as pure DNA (transfection) by, for example, precipitation with calcium phosphate (Graham and vander Eb (1973) *Virology* 52:466) or strontium phosphate (Brash et al. (1987) *Mol. Cell. Biol.* 7:2013), electroporation (Neumann et al. (1982) *EMBO J.* 1:841), lipofection (Felgner et al. (1987) *Proc. Natl. Acad. Sci. USA* 84:7413), DEAE dextran (McCuthan et al. (1968) *J. Natl. Cancer Inst.* 41:351), microinjection (Mueller et al. (1978) *Cell* 15:579), protoplast fusion (Schafner, (1980) *Proc. Natl. Acad. Sci. USA* 77:2163-2167), biolistics, e.g., pellet guns (Klein et al. (1987) *Nature* 327:70) or Gene guns. Alternatively, the cDNA, or fragments thereof, can be introduced by infection with virus vectors. Systems are developed that use, for example, retroviruses (Bernstein et al. (1985) *Gen. Engr'g* 7:235), adenoviruses (Ahmad et al. (1986) *J. Virol.* 57:267), or Herpes virus (Spaete et al. (1982) *Cell* 30:295). Polynucleotides that encode proteins, such as fusion proteins, can also be delivered to target cells in vitro via non-infectious systems, such as liposomes.

Using the above techniques, the expression vectors containing a polynucleotide encoding a monomeric fusion polypeptide as described herein or cDNA, or fragments or variants or mutants thereof, can be introduced into human cells, mammalian cells from other species or non-mammalian cells as desired. The choice of cell is determined by the purpose of the treatment. For example, monkey COS cells (Gluzman (1981) *Cell* 23:175-182) that produce high levels of the SV40 T antigen and permit the replication of vectors containing the SV40 origin of replication can be used. Similarly, Chinese hamster ovary (CHO), mouse NIH 3T3 fibroblasts or human fibroblasts or lymphoblasts can be used.

Methods of Enhancing an Antigen Specific Immune Response

The enhancement of an antigen-specific immune response in a subject (e.g., a mammalian subject, such as a human subject) by engaging the OX-40 receptor on CD4+ T-cells during or after antigen activation can be accomplished using a wide variety of methods. The method of choice will primarily depend upon the type of antigen against which it is desired to enhance the immune response, and various methods available are discussed below. Whatever method is selected, the trimeric OX-40L fusion protein should be administered to the animal such that it is presented to T-cells of the subject during or shortly after priming of the T-cells by the antigen. In an exemplary method a trimeric OX-40L fusion protein comprising the polypeptide represented by SEQ ID NO: 8 is administered.

Since the activation of T-cells generally takes place within about 7 days after an antigen is presented to the immune system (and often within about 24-48 hours of exposure to antigen), it is generally preferable to administer the trimeric OX-40L fusion protein to the subject by the selected method within about 10 days after the subject's immune system is exposed to the antigen. Typically, the trimeric OX-40L fusion protein is administered either concurrently with, or within about 24 hours of exposure to antigen. Nonetheless, later administration, e.g., within about 48 hours, within about 72 hours, up to within about 4-10 days of exposure to antigen is possible. Where the trimeric OX-40L fusion protein is administered simultaneously with the antigen, it is generally advantageous to administer a form of the agent which has enhanced stability (such as, increased half-life, resistance to proteolysis, etc.) in the body so that the agent will remain in the circulatory system for a sufficient period of time to engage with OX-40 receptor during or after antigen priming. Favorably, the trimeric OX-40L fusion protein described herein, including a trimerization domain and an immunoglobulin domain, exhibits such enhanced stability as compared to an isolated extracellular OX-40L domain or a monomeric OX-40L fusion polypeptide. Within the purview of the present disclosure, a polypeptide domain can be substituted for the immunoglobulin domain so long as the selected polypeptide domain maintains a similar increase in stability.

One of ordinary skill in the art can determine the half-life of any selected OX-40L fusion polypeptide using standard methods. For example, after administration of the fusion polypeptide by intravenous injection, a small blood sample can be removed from the subject, with subsequent samples being taken every 6-24 hours over the period of about 10 days. Thereafter, the concentration of the fusion polypeptide present in each sample is determined (e.g., using standard immunological quantification methods, such as those discussed in Harlow & Lane (1988), e.g., ELISA). The half-life of the fusion polypeptide is defined as that time point at which the concentration of the agent falls to 50% of that in the first sample measurement.

In some situations, for example where the antigen is presented to the immune system over an extended duration (for example, in cancer patients), the trimeric OX-40L fusion protein can be administered more than 7 days after the immune system is first exposed to the antigen. For example, following surgical removal of a primary tumor from a patient, a trimeric OX-40L fusion protein can be administered to enhance the immune response to tumor antigens present on metastases, thereby promoting the clearance of such metastases from the body. In such a situation, administration of the trimeric OX-40L fusion protein will usually occur more than 7 days after the immune system of the patient was first exposed to the tumor antigens, but will nevertheless be present subsequently when the antigens are being presented to T-cells.

In contrast, when the antigen to which an immune response is desired is a soluble antigen, it is generally desirable to administer the trimeric OX-40L fusion protein simultaneously with, or within approximately 24 to 48 hours of, exposure to the antigen.

While the molecule which engages the OX-40 receptor will be in the form of a protein, that is, as an assembled hexameric complex including two trimeric OX-40L fusion proteins, the preparation administered to the mammal can take a number of forms, including a preparation of a purified trimeric OX-40L fusion protein, preparation of a purified OX-40L fusion polypeptide, preparation of a nucleic acid molecule which encodes the trimeric OX-40L fusion protein, a cell or a virus which expresses the trimeric OX-40L fusion protein, or a preparation derived from such a cell or virus.

In its simplest form, the preparation administered to the mammal is a hexameric OX-40L fusion protein (e.g., made up of "dimerized" trimers), administered in conventional dosage form, and preferably combined with a pharmaceutical excipient, carrier or diluent. Suitable pharmaceutical carriers can be solids or liquids, and can include buffers, anti-oxidants such as ascorbic acid, other polypeptides or proteins such as serum albumin, carbohydrates, chelating agents and other stabilizers and excipients. Suitable solid carriers include lactose, magnesium stearate, terra alba, sucrose, talc, stearic acid, gelatin, agar, pectin, acacia and cocoa butter. The amount of a solid carrier will vary widely depending on which carrier is selected, but preferably will be from about 25 mg to about 1 g per dose of active agent. Suitable liquid carriers include normal saline and neutral buffered saline, optionally with suitable preservatives, stabilizers and excipients. The carrier or diluent can also include time delay material well known to the art such as, for example, glycerol distearate, either alone or with a wax. The foregoing examples of suitable pharmaceutical carriers are only exemplary and one of skill in the art will recognize that a very wide range of such carriers can be employed. Liposome-based delivery systems can also be employed to deliver trimeric OX-40L fusion proteins. Liposome-based systems, which can be employed to provide a measured release of the agent over time into the bloodstream, are well known in the art and are exemplified by the systems described in U.S. Pat. Nos. 4,356,167; 5,580,575; 5,595,756; and 5,188,837, and documents cited therein.

The formulation of the trimeric fusion protein, such as a trimeric OX-40L fusion protein, with a pharmaceutical carrier can take many physical forms, but is preferably a sterile liquid suspension or solution, suitable for direct injection. Preferably, the subject will be administered the trimeric OX-40L fusion protein in a formulation as described above (for example, in combination with a pharmaceutical carrier), wherein the formulation includes a clinically effective amount of the fusion protein.

As used herein, "a therapeutically effective amount" is an amount that results in a therapeutically significant effect. This nature of this effect will vary with the context in which the trimeric OX-40L fusion protein is being used, for example, whether the fusion protein is being administered to treat an existing condition (for example, to treat an infectious disease, or cancer) or as a prophylactic (to prevent or reduce the risk of disease or cancer, e.g., recurrence of a tumor or metastasis of a tumor) agent. If the trimeric OX-40L fusion protein is being administered to a cancer patient, it will be appreciated that any improvement in the patient's condition is therapeutically significant. Hence, in such a situation, "a therapeutically effective amount" encompasses amounts of the trimeric OX-40L fusion protein that result in at least partial remission of the cancer as well as amounts which slow or limit the further progression of the cancer. Similarly, in the therapeutic context where the agent is being used to enhance the immune response of a patient to an infectious agent, such as a virus or a bacterium, where the patient is already infected with the agent, a therapeutically effective amount can produce a therapeutic effect, meaning an effect which results in some degree of recovery from the infection or amelioration of the clinical symptoms.

In the prophylactic context, such as vaccination, a therapeutically effective amount of a trimeric OX-40L fusion protein can provide an enhancement of the immune response to the target antigen, that is, produce an immune response greater than would be presented absent administration of the trimeric OX-40L fusion protein. Quantification of the immune response arising from a vaccination can be achieved in any standard way, e.g., measurement of serum antibody titer for level and/or duration against any convenient test antigen, and/or lymphoproliferation in response to test antigen in vitro.

It will be appreciated that a therapeutically effective dose of a trimeric OX-40L fusion protein will vary depending on the clinical context (e.g., whether the agent is being used therapeutically or prophylactically), the characteristics of the subject (age, weight, other medications being taken, etc.) and the severity of the condition. Thus, the assessment of a therapeutically effective dosage will ultimately be decided by a physician, veterinarian, or other health care worker familiar with the subject. Typically, administering a trimeric OX-40L fusion protein to a subject according to the methods of the present disclosure will involve administration of from about 10 ng to 1 g of trimeric OX-40L fusion protein per dose, with single dose units of from about 10 ng to 100 mg being commonly used, and specific dosages of up to 1 mg or 10 mg also being within the commonly used range.

The trimeric OX-40L fusion protein can be administered to a subject through a number of routes, including subcutaneously or intravenously or, where the subject has a tumor, directly into the tumor site. The agent can be the sole active ingredient in the composition, or it can be combined with other agents having a beneficial effect, such as an interferon or other immune-stimulatory molecules.

In the prophylactic (vaccine) context, the trimeric OX-40L fusion protein is often administered to a subject in combination with a conventional vaccine preparation or formulation, such as a vaccine preparation comprising bacterial or viral antigens. The trimeric OX-40L fusion protein can be combined with the conventional vaccine, or can be administered as a separate preparation along with the conventional vaccine. For example, where the trimeric OX-40L fusion protein is administered separately, it is typically administered within about a week of the vaccine being administered. Conventional vaccine preparations suitable for use in the present disclosure include those prepared with purified bacterial antigens, heat killed bacteria, subunit vaccines and viral vaccines based on live or attenuated virus. A vaccine preparation can include a pharmaceutical carrier and/or adjuvant.

Where the trimeric OX-40L fusion protein is administered to the subject in a single preparation with the vaccine antigens, the preparation can be formulated simply by mixing a therapeutically effective amount of a trimeric OX-40L fusion protein with the antigen preparation. Alternatively, the trimeric OX-40L fusion protein can be produced along with the antigen. For example, where the antigen to be administered as a vaccine is a bacterial antigen or a mixture of bacterial antigens, the bacterium from which the antigen preparation is prepared can be a transgenic bacterium which expresses the trimeric OX-40L fusion protein. In such a situation, the trimeric OX-40L fusion protein is directly obtained in combination with the bacterial antigens. Similarly, vaccines comprising tumor antigens and trimeric OX-40L fusion protein can be prepared from tumor cells which express the trimeric OX-40L fusion protein. Methods of expressing proteins such as OX-40L fusion polypeptides in transgenic prokaryotic and eukaryotic cells are well known to those of ordinary skill in the art, and are described in standard laboratory texts such as Sambrook and Ausubel, cited above.

In other embodiments, the immune response of a subject to a particular antigen is enhanced by administering to the subject a nucleic acid molecule that encodes an OX-40L fusion polypeptide that is capable of forming a trimeric OX-40L fusion protein. Such a nucleic acid molecule is preferably administered either as a component of a cell, or as part of a viral genome. Alternatively, the nucleic acid encoding the OX-40L fusion polypeptide can be administered to the subject as a "naked" nucleic acid molecule.

For example, a nucleic acid molecule encoding an OX-40L fusion polypeptide can be introduced into an attenuated bacterium (that is, a form of the bacterium that does not cause significant disease when administered to a subject) in a plasmid vector such that the trimeric OX-40L fusion protein is secreted by the bacterium. The bacterium can be administered to the mammal in the same manner as a conventional attenuated bacterial vaccine.

Alternatively, the nucleic acid molecule encoding the trimeric fusion protein, such as nucleic acids encoding trimeric OX-40L fusion proteins, can be introduced into the genome of a virus that is used as a live attenuated vaccine. Attenuated viruses include those in which an essential gene has been deleted, as described in U.S. Pat. Nos. 5,665,362 and 5,837,261. Viruses suitable for this purpose include DNA viruses, such as adeno, herpes, papova, papilloma and parvo viruses, as well as RNA viruses such as poliovirus and influenza virus. Methods of preparing viruses carrying heterologous nucleic acid sequences that can be used as viral vaccines are described in U.S. Pat. Nos. 5,665,362 and 5,837,261 (supra); 5,338,683 and 5,494,807.

In another embodiment, a nucleic acid encoding an OX-40L fusion polypeptide capable of forming a trimeric OX-40L fusion protein can be introduced into a tumor cell. In many cancer patients, tumor cells escape detection by the immune system by mechanisms such as down-regulating MHC and/or co-stimulatory molecule expression. Accordingly, one method of treatment is to remove tumor cells from the patient and introduce into them nucleic acids encoding, for example, MHC class II, the co-stimulatory molecule B7 and the stimulatory/adhesion molecule CD2 (see, for example, European Patent Application publication number EP 733,373, and references cited therein). Similarly, a nucleic acid encoding a OX-40L fusion polypeptide can be introduced into tumor cells to increase the immunogenicity of the tumor cells.

All types of tumor are potentially amenable to treatment by this approach including, for example, carcinoma of the breast, lung, pancreas, ovary, kidney, colon and bladder, as well as melanomas, sarcomas and lymphomas. Nucleic acid molecules encoding an OX-40L fusion polypeptide capable of forming a trimeric OX-40L fusion protein are incorporated into a vector suitable for expression of the OX-40L fusion polypeptide in tumor cells. Suitable vectors include plasmid, cosmid and viral vectors, such as retroviruses, adenoviruses and herpes viruses. Disabled viruses, such as those described in U.S. Pat. Nos. 5,665,362 and 5,837,261 can be employed for this purpose.

In addition to a nucleic acid molecule encoding a trimeric OX-40L fusion protein polypeptide, other nucleic acid molecules can also be introduced into the vector to further enhance the immunogenic effect. By way of example, such other nucleic acid molecules include nucleic acids encoding MHC class II proteins (including α and β subunits), and other co-stimulatory molecules, such as B7.1 and B7.2. If desired, a nucleic acid molecule encoding a selectable marker can also be introduced into the vector, such that those tumor cells successfully transformed with the vector can be readily selected.

The vector is then introduced into the tumor cell by one of a range of techniques, such as electroporation, lipofection, co-cultivation with virus-producing cells, or other standard means. In an exemplary embodiment, the tumor cells are cells removed from the subject (patient) to be treated. Alternatively the tumor cells can be cells from a tumor cell line, such as the human tumor cell lines available from the American Type Culture Collection (ATCC).

Optionally, the cells can be screened to identify those cells into which the vector was introduced. Screening can be accomplished by any of a variety of procedures, including selecting for expression of the selectable marker if one is used, or screening for expression of the trimeric OX-40L fusion protein on the surface of the cells. This latter procedure can be conveniently performed by flow cytometry using a labeled antibody specific for the extracellular portion of OX-40L or for the Ig domain.

The tumor cells are subsequently administered to the subject in combination with a suitable carrier such as buffered water, saline, or glycine. In one embodiment, where the tumor cells are cells originally removed from the patient, they are attenuated before being administered to the subject. An attenuated cell is one which is metabolically active but which is no longer able to proliferate. Methods for attenuating tumor cells are well known and include those described in EP 733, 373.

In an alternative embodiment, cell membranes from the tumor cells, which include the trimeric OX-40L fusion protein can be administered to the patient instead of intact tumor cells. A cell membrane preparation can readily be prepared by disrupting or lysing the cells using standard techniques, such as a French Press, freeze-thawing, or sonication. Following disruption of the cells, a membrane enriched fraction is obtained by centrifugation.

Alternatively, nucleic acid molecules encoding an OX-40L fusion polypeptide that is capable of assembly into a trimeric OX-40L fusion protein can be administered directly to a subject in the form of "naked" DNA, such that expression of the OX-40L fusion polypeptide occurs in the subject's body. Methods of administering naked DNA to animals in a manner to cause expression of that DNA in the body of the animal are well known, and are described, for example, in U.S. Pat. Nos. 5,620,896; 5,643,578 and 5,593,972, and references cited therein.

The present disclosure also encompasses other immunotherapy methods for treating conditions such as cancer, including adoptive immunotherapy. As is known in the art, adoptive immunotherapy involves obtaining lymphoid cells exposed to a particular antigen, culturing those cells ex vivo under conditions whereby the activity of the cells is enhanced, and then administering the cells to an individual. The lymphoid cells are preferably T-cells removed from a cancer patient, for example T-cells from a draining lymph node. As discussed above, engagement of the OX-40 receptor on these cells with a trimeric OX-40L fusion protein will stimulate these cells and enhance memory T cell generation. Accordingly, the methods provide a form of adoptive immunotherapy in which the incubation of lymphoid cells ex vivo is performed in a medium containing a trimeric OX-40L fusion polypeptide prior to administration of the cells to a patient. The technical details of methods for obtaining lymphoid cells, ex vivo cultivation of such cells with immune stimulants, and administration to patients are known in the field and are described, for example in U.S. Pat. Nos. 4,690,915; 5,229,115; 5,631,006 and 4,902,288, and references cited therein.

EXAMPLES

Example 1

Production of an OX-40L Fusion Polypeptide

An exemplary multimeric human Ig:OX-40L fusion protein (shown schematically in FIG. 1) was prepared in the following manner. The construct involved assembling four domains: a signal sequence, the Fc domain of human IgG1, an isoleucine zipper derived from yeast GCN4 transcription factor, and finally at the C-terminus, the complete extracellular domain of human OX-40L.

Figure 2:
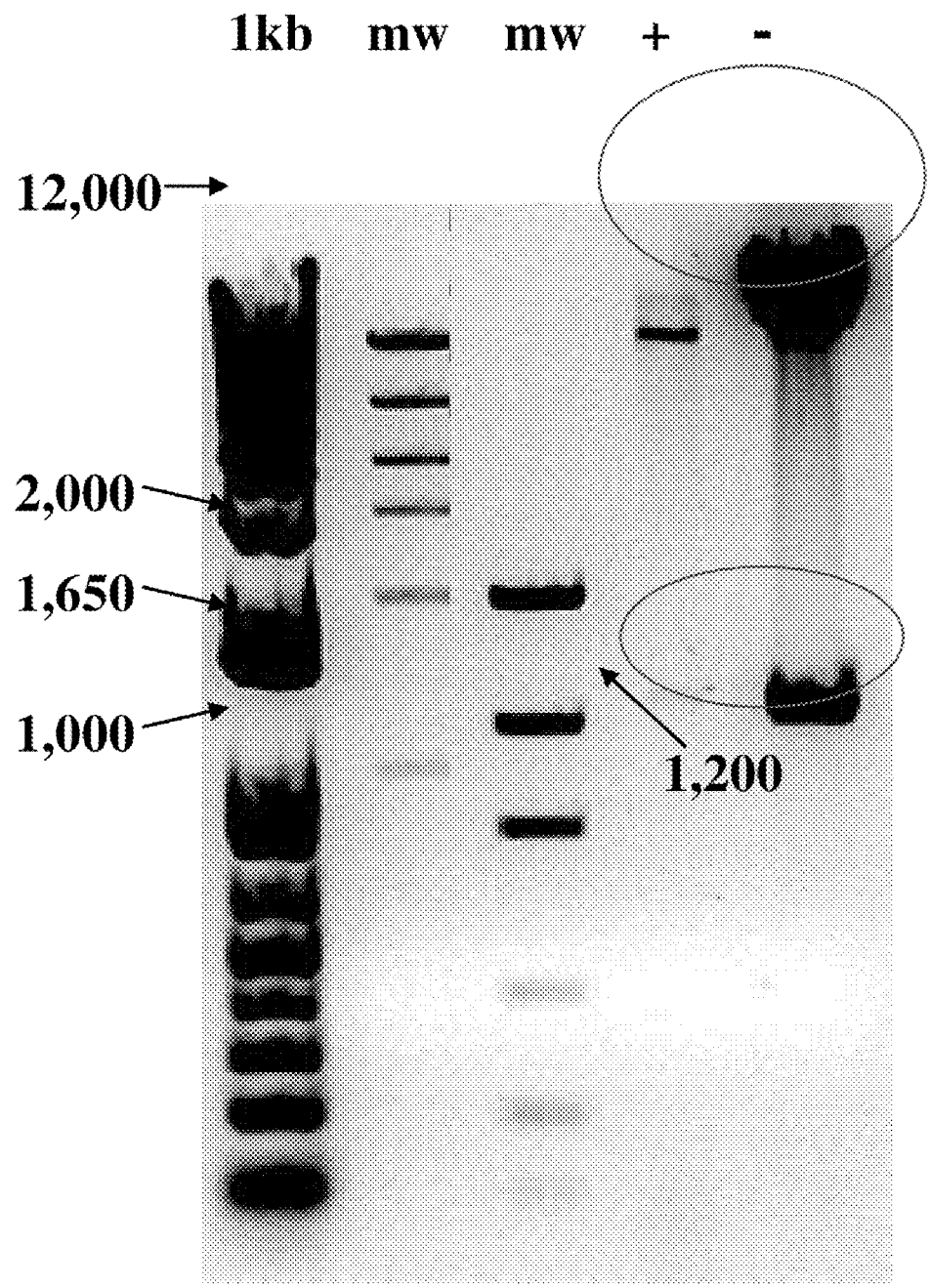
FIG. 2 is an image of an agarose gel illustrating the correctly sized Fc/ILZ/OX-40L insert and vector.

The starting point was a pCMVFlag.1-TriZP-BAFF. TriZP is the isoleucine zipper and is referred to as ILZ The BAFF domain in this plasmid is flanked by Eco RI (5') and Xho I (3') restriction sites. The complete extracellular domain (C-terminal to the transmembrane domain) of OX-40L was amplified from a plasmid containing the full-length human OX-40L coding sequence by PCR. For this reaction, the 5' primer contained a flanking Eco RI site and an A>T change in the coding sequence to remove an interfering Eco RI site 26 bases down stream. The 3' primer contained a flanking Xho I site, a stop codon and an A>T change 13 bases from the Xho I site to remove another interfering Eco RI site at this position. The first A to T mutation resulted in the substitution of isoleucine with phenylalanine (e.g., as shown in SEQ ID NO: 2, $9^{th}$ amino acid). The second A to T mutations did not alter the amino acid sequence of the encoded OX-40L domain. The amplified OX-40L extracellular domain was cleaved with Eco RI and Xho I, purified by agarose gel electrophoresis (gel purified) and cloned into the Eco RI/Xho I site vacated by the BAFF domain in the pCMV vector. The now contiguous ILZ:OX-40L domains were amplified by PCR from this new pCMV plasmid using a 5' primer containing a flanking Sac I site and the same 3' primer used to amplify the OX40L domain initially. TOPO TA cloning was used to ligate, via topoisomerase, the amplified product into the pCR 2.1 plasmid (Invitrogen, Carlsbad, Calif.). The same strategy was employed to amplify and clone the human Fc-γ domain from IgG1 into pCR 2.1. The Fc-γ fragment of IgG1 was previously modified by converting the Cys residue (tgt) in the hinge region to Thr (acc) corresponding to base 799 in BC 041037. The 5' primer included a flanking Nhe I site, an additional base, A, to maintain reading frame for the next step in cloning and the coding sequence started with the mutated Thr codon. The 3' primer contains a flanking Sac I site and the coding sequence ends with the C-terminal Lys (aaa) of the IgG1. The ILZ-OX-40L insert was excised from pCR 2.1 by cleavage with Sac I and Xho I, gel purified, and cloned into the Fc-γ pCR2.1 also cut with Sac I and Xho I. This results in the contiguous positioning of Fc-gamma, ILZ and OX-40L and the insertion of the dipeptide, Leu-Gln, encoded by the added Sac I site between Fc-γ and ILZ. For expression in mammalian cells the construct, FC-ILZ-OX-40L, was cloned into a modified version of the pCEP4 expression vector (Invitrogen). The plasmid, designated pCEP D4-7, was modified to include the signal sequence of the basement membrane protein BM40 adjacent to the multiple cloning site. pCEP4 controls transcription from the CMV promoter. Expression of the EBNA gene from Epstein Barr virus promotes autosomal replication of the plasmid resulting in high copy number. The Fc-ILZ-OX-40L insert was cleaved from pCR2.1 using Nhe I and Xho I, gel purified and ligated into pCEP D4-7 also cut with Nhe I and Xho I. The final construct was analyzed by restriction analysis, as shown in FIG. 2. The insert was sequenced to confirm the authenticity of the encoded fusion protein.

Example 2

Production of an OX-40L Fusion Polypeptide

Figure 3B:
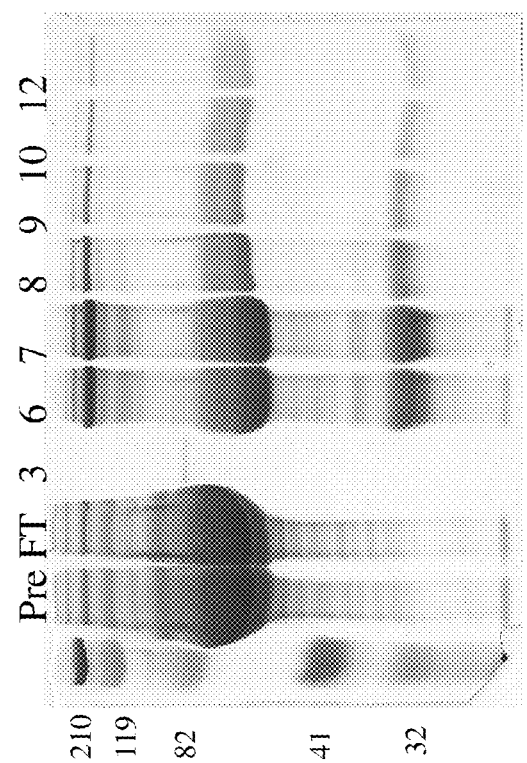
FIG. 3B is an image of a 10% acrylamide gel run under reducing conditions and stained with Coomassie blue, illustrating maximal elution in peaks 6-7.
Figure 3A:
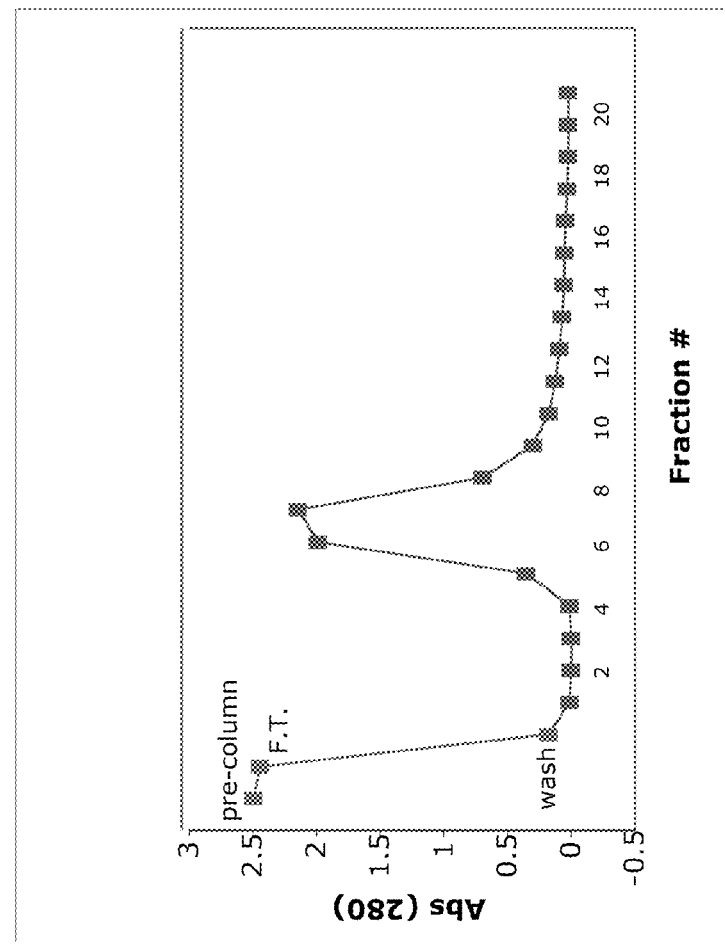
FIG. 3A is a line graph illustrating the quantity of fusion polypeptide eluted in each elution fraction after binding to a Protein G column

In order to produce recombinant multimeric OX-40L fusion protein, the Fc-ILZ-OX-40L fusion construct was introduced into HK 293 cells by transfection with lipofectamine. The HK 293 cell line is a well-established culture line used extensively for mammalian protein expression. The pCEP D4-7 contains a hygromycin resistance gene permitting selection of stably transfected colonies of 293 cells in the presence of hygromycin. Because pCEP D4-7 replicates autosomally, all of the hygromycin resistant cells were pooled and expanded in cell culture to monitor Fc-ILZ-OX-40L synthesis. For protein production the cells were cultured in a laboratory scale bioreactor (Cell-Max). The fusion protein was purified by Protein G affinity chromatography. An exemplary protein G elution profile is shown in FIGS. 3A and B. As shown in FIG. 3B, maximal elution was observed in fractions 6 and 7. The identity of the eluted protein was confirmed by immunoreactivity using anti human IgG (FIGS. 4A and B) and anti-human OX-40 ligand antibodies (FIGS. 4C and D). Under reducing conditions, the predominant product was observed to migrate at approximately 43 kD, consistent with a monomeric fusion polypeptide. Under non-reducing conditions, higher molecular weight species were observed. A strong band was observed at 86 kD consistent with formation of dimers linked by disulfide bonds between two Fc domains. Assembly into trimers involves noncovalent interactions between OX-40L and trimerization domains, and leaves one unpaired Fc domain. Association between unpaired Fc domains in two trimeric OX-40L fusion proteins results in the formation of hexamer under native conditions. However, on non-reducing SDS PAGE gels nothing larger than dimers is observed following elution in acid pH.

Figure 5:
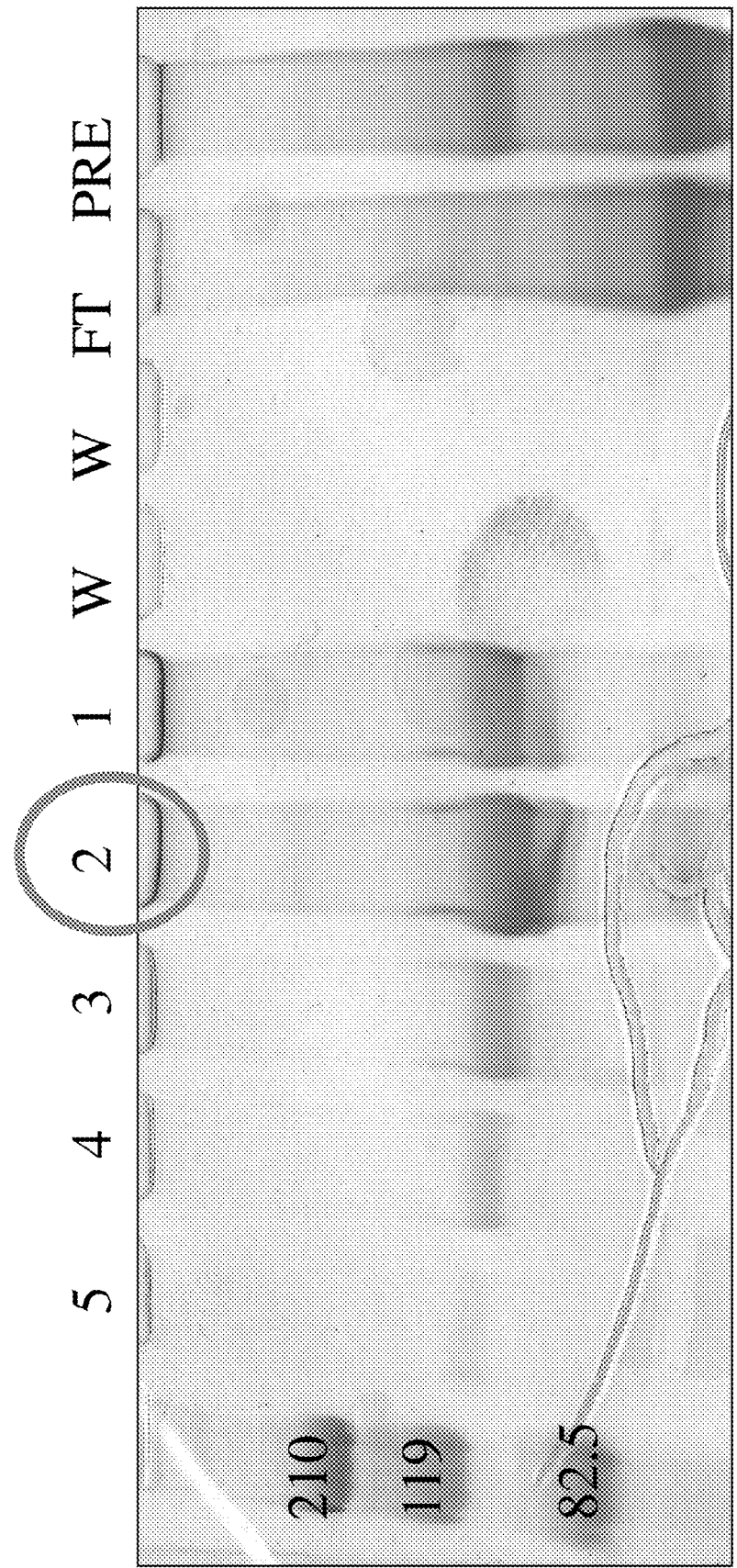
FIG. 5 is a digital image of a coomassie stained acrylamide gel illustrating the elution profile in ActiSep elution medium.

Although analysis of F-ILZ-OX-40L after elution at acid pH indicated appropriate covalent assembly of subunits, analysis by size exclusion chromatography under non-denaturing conditions indicated that acid pH induced non-covalent aggregation of the protein into higher order structures. To prevent this aggregation, the fusion protein was eluted from the protein-G column using ActiSep Elution Medium (Sterogene, Carlsbad, Calif.), buffered at a pH of between 4 and 7. This single step yielded a high degree of purification (FIG. 5) and generated the material subsequently analyzed for structure and for biological activity.

Figure 6:
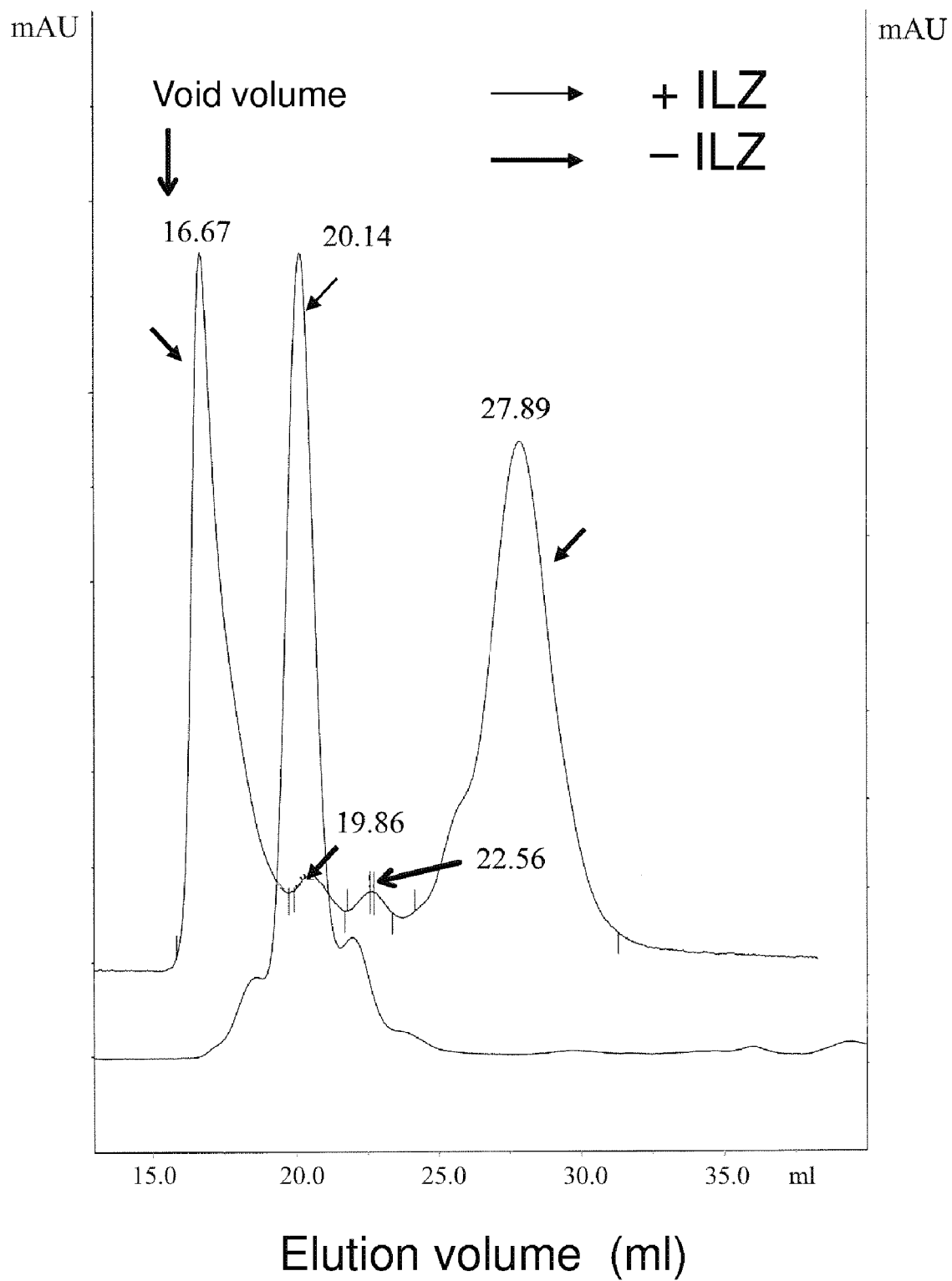
FIG. 6 is a graph illustrating results of size exclusion chromatography comparing human OX-40L fusion proteins with and without a trimerization domain.

The contribution of the ILZ domain to the folding recombinant Fc:OX-40L fusion protein was demonstrated by comparing the elution profile from size exclusion chromatography of Fc:ILZ:OX-40L and Fc:OX-40L as shown in FIG. 6. Fc:ILZ:OX-40L elutes as a largely homogeneous and symmetrical peak at about 20 ml, corresponding to an equivalent sphere with a mass of about 570 kDa. This is about twice the expected mass but this is likely due to the asymmetric structure imparted by the three domains of the fusion protein. In contrast, in the absence of the ILZ domain, very little of the purified protein elutes at 20 ml and instead elutes as large aggregates in the void volume or as low molecular weight components likely to be unassembled monomers. This indicates that for the human molecule, the ILZ trimerization domain is involved in productive folding of the recombinant extracellular receptor-binding domain of OX-40L.

Example 3

Trimeric OX-40L Fusion Protein Induced T-Cell Proliferation

Figure 7:
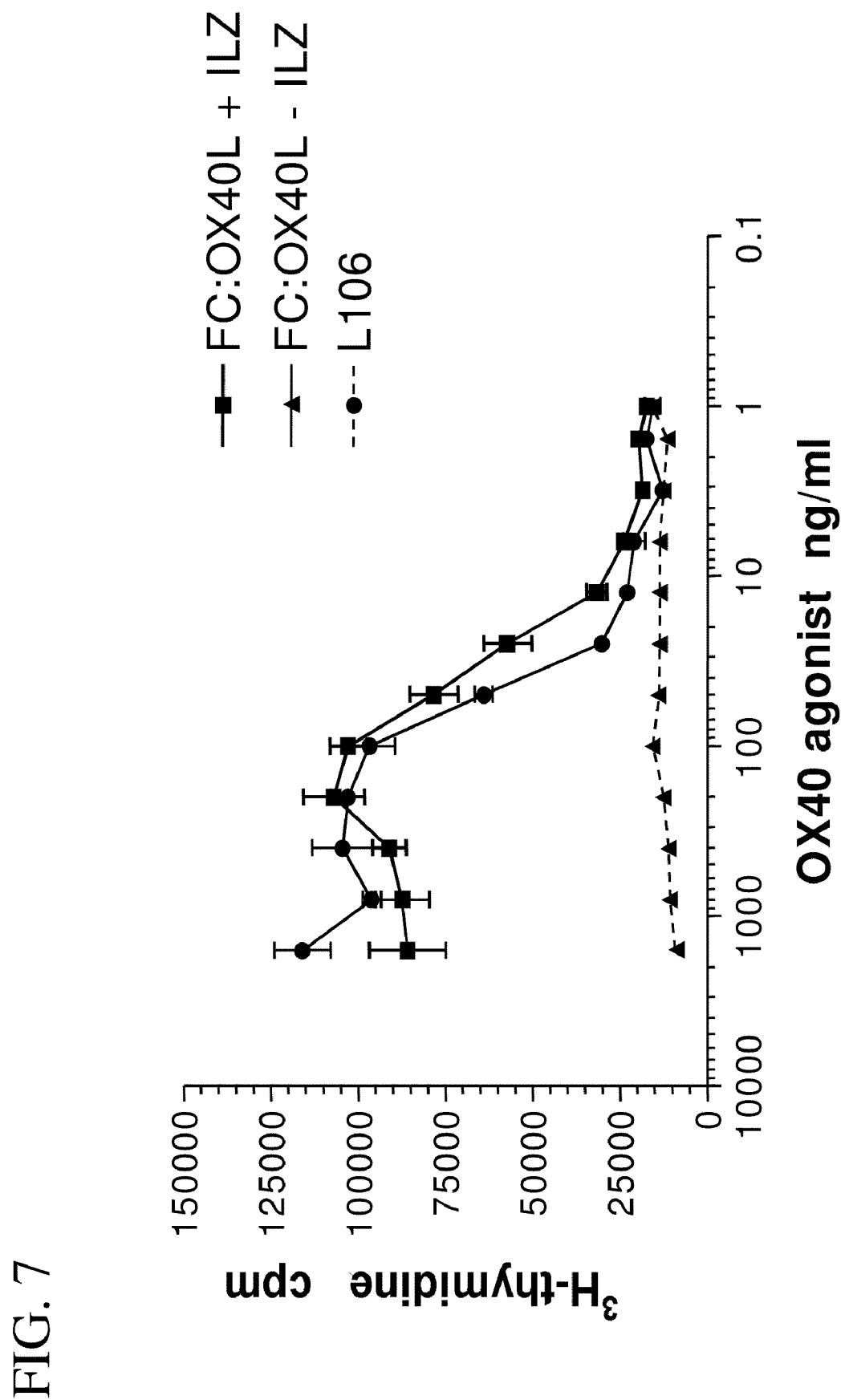
FIG. 7 is a graph illustrating proliferation of T cells in response to exposure to multimeric human OX-40L fusion protein.

The functional contribution of the ILZ domain was tested by comparing the costimulatory activity of Fc:ILZOX-40L with Fc:OX-40L in a proliferation assay in vitro (FIG. 7). FIG. 7 illustrates the biological activity of recombinant human Fc:ILZOX-40L with and without the ILZ domain. The recombinant protein was tested for biological activity in vitro by costimulation of CD4$^+$ T-cell proliferation in response to anti-CD3. Ninety-six-well culture plates were coated with goat anti-human Ig and goat anti-mouse Ig capture antibodies, both at 2 µg/ml. The plates were incubated with mouse anti-human CD3 at 2 ng/ml followed by serial two-fold dilutions of recombinant OX-40L fusion protein (1600 to 3 ng/ml). Purified human CD4 T-cells that had been activated with PHA and cultured for four days with IL2 (10 U/ml) were washed and added to each well at $5 \times 10^4$ cells per well. The cells were labeled with $^3$H-thymidine for the last 16 hours of a 62 hour culture, harvested and counted. The results, shown in FIG. 7, are presented as mean CPM with standard deviation calculated from triplicate wells. The results indicate that the trimeric OX-40L fusion protein containing the ILZ domain produced a dose-dependent costimulation/stimulation (mitogenesis) of the CD4$^+$ T-cells while the construct lacking the ILZ domain was essentially inactive.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A fusion polypeptide comprising in an N-terminal to C-terminal direction:
   an immunoglobulin domain, wherein the immunoglobulin domain comprises an Fc domain;
   a trimerization domain, wherein the trimerization domain comprises a coiled coil trimerization domain; and
   a receptor binding domain, wherein the receptor binding domain is an OX-40 receptor binding domain,
   and wherein the fusion polypeptide self-assembles into a trimeric fusion protein.

2. The fusion polypeptide of claim 1, wherein the fusion protein is capable of binding to the OX-40 receptor and stimulating at least one OX-40 mediated activity.

3. The fusion polypeptide of claim 1, wherein the OX-40 receptor binding domain comprises an extracellular domain of OX-40 ligand (OX-40L).

4. The fusion polypeptide of claim 3, wherein the OX-40 mediated activity is CD4+ T cell proliferation.

5. The fusion polypeptide of claim 3, wherein the OX-40 receptor binding domain comprises a polypeptide sequence at least 95% identical to the amino acid sequence set forth as SEQ ID NO: 2.

6. The fusion polypeptide of claim 1, wherein the trimerization domain is a TRAF2 or a Matrilin-4 trimerization domain.

7. The fusion polypeptide of claim 6, wherein the trimerization domain comprises a TRAF2 trimerization domain.

8. A multimeric fusion protein comprising a plurality of the fusion polypeptides of claim 1.

9. The multimeric fusion protein of claim 8, consisting of three or six fusion polypeptides.

10. A recombinant nucleic acid comprising a polynucleotide sequence that encodes the fusion polypeptide of claim 1.

11. A composition comprising the fusion polypeptide of claim 1, or a nucleic acid encoding the fusion polypeptide, and a pharmaceutically acceptable carrier.

12. A fusion polypeptide comprising in an N-terminal to C-terminal direction:
   an immunoglobulin Fc domain comprising the amino acid sequence set forth as SEQ ID NO: 6;
   a TRAF2 trimerization domain; and
   an OX-40 receptor binding domain comprising the amino acid sequence set forth as SEQ ID NO: 2,
   wherein the fusion polypeptide self-assembles into a trimeric fusion protein.

13. The fusion polypeptide of claim 12, wherein the trimeric fusion protein consists of three or six fusion polypeptides.

14. A method of enhancing T-cell proliferation in a subject, the method comprising:
   administering to a subject exposed to an antigen, a therapeutically effective amount of the fusion protein of claim 1, thereby enhancing T-cell proliferation in response to the antigen by the subject.

15. The method of claim 14, wherein the subject is a human subject.

16. The method of claim 14, wherein the fusion protein comprises in an N-terminal to C-terminal direction:

a dimerization domain comprising an immunoglobulin Fc domain;

a TRAF2 trimerization domain; and an OX-40 receptor binding domain comprises a polypeptide sequence at least 95% identical to the amino acid sequence set forth as SEQ ID NO: 2, wherein the fusion polypeptide self-assembles into a trimeric fusion protein.

17. The method of claim 14, wherein the subject is exposed to the antigen prior to administering the fusion protein or wherein subject is exposed to the antigen and administered the trimeric OX-40L fusion protein at the same time.

18. The fusion polypeptide of claim 7, further comprising a signal sequence, a linker sequence, an amino acid tag, a label, or a polypeptide sequence that facilitates purification.

19. The fusion polypeptide of claim 1, wherein the Fc domain comprises the amino acid sequence set forth as SEQ ID NO: 6.

* * * * *